United States Patent [19]

Balasubramanian

[11] Patent Number: 5,382,584
[45] Date of Patent: Jan. 17, 1995

[54] ADENOSINE RE-UPTAKE INHIBITING DERIVATIVES OF DIPHENYL OXAZOLES, THIAZOLES AND IMIDAZOLES

[75] Inventor: Neelakantan Balasubramanian, Bristol, Conn.

[73] Assignee: Bristol-Myers Squibb Company, New York, N.Y.

[21] Appl. No.: 206,572

[22] Filed: Mar. 4, 1994

Related U.S. Application Data

[63] Continuation-in-part of Ser. No. 48,338, Apr. 15, 1993, abandoned, which is a continuation-in-part of Ser. No. 923,399, Jul. 31, 1992, abandoned.

[51] Int. Cl.$^6$ .................. A61K 31/495; C07D 413/06; C07D 417/06
[52] U.S. Cl. ..................................... 514/252; 544/369
[58] Field of Search .................... 544/369; 514/252

[56] References Cited

U.S. PATENT DOCUMENTS

| | | | |
|---|---|---|---|
| 3,267,104 | 8/1966 | Hermans et al. | 260/268 |
| 4,020,082 | 4/1977 | Marchetti | 424/250 |
| 4,101,660 | 7/1978 | Inoue et al. | 424/250 |
| 4,766,125 | 8/1988 | Van Daele | 514/255 |
| 4,948,796 | 8/1990 | Hiraiwa et al. | 514/254 |

FOREIGN PATENT DOCUMENTS

| | | |
|---|---|---|
| 0068544 | 1/1983 | European Pat. Off. . |
| 0285219 | 10/1988 | European Pat. Off. . |
| 0388909 | 9/1990 | European Pat. Off. . |
| WO91/04032 | 4/1991 | European Pat. Off. . |
| 2459242 | 1/1981 | France . |

OTHER PUBLICATIONS

Inoue et al, "2-Aminomethyl-5-phenyloxazoles", Chemical Abstracts, vol. 91 (1979), pp. 707, paragraph: 91:56986x.

Inoue et al, "2-Aminomethyl-5-phenyloxazoles", Chemical Abstracts, vol. 91 (1979), pp. 707-708, paragraph: 91:56987y.

Primary Examiner—Cecilia Tsang
Attorney, Agent, or Firm—Richard P. Ryan

[57] ABSTRACT

A series of 1-piperazinyl-N-phenylacetamide derivatives of 4,5-diphenyl-oxazoles, thiazoles, and imidazoles which are novel adenosine transport inhibitors have been found to provide effective antiischemic protection for CNS and cardiac tissue, particularly neurons. A method of treatment to protect against CNS ischemia, such as that resulting from trauma, stroke, or other ischemic conditions, comprises administration of these novel compounds to an individual in need of such treatment.

16 Claims, No Drawings

ADENOSINE RE-UPTAKE INHIBITING DERIVATIVES OF DIPHENYL OXAZOLES, THIAZOLES AND IMIDAZOLES

CROSS REFERENCE TO RELATED APPLICATION

This is a continuation-in-part application of Ser. No. 08/048,338 filed Apr. 15, 1993 now abandoned, which is itself a continuation-in-part application of Ser. No. 07/923,399 filed Jul. 31, 1992 and now abandoned.

BACKGROUND OF THE INVENTION

This invention pertains to N-piperazineacetamide derivatives of 4,5-diphenyl-oxazoles, thiazoles and imidazoles having drug and bio-affecting properties and to their preparation and use. In particular the compounds of this invention are novel adenosine reuptake inhibitors that are neuroprotective under conditions of anoxia, ischemia or stroke.

Related art in terms of chemical structure may be represented by the following references.

Inoue, et al., in U.S. Pat. No. 4,101,660 disclosed and claimed a series of antiinflammatory and analgesic oxazole compounds (1)

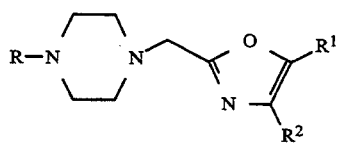

in which $R^1$ is phenyl, $R^2$ is hydrogen and R is hydroxyethyl. The series was extended to diphenyl derivatives ($R^1=R^2=$phenyl) in Chem. Abstr. 91:56986x and to piperidine derivatives (R=piperidinylalkyl) in Chem. Abstr. 91:56987y.

Various N-aryl-piperazinealkanamides of structure (2)

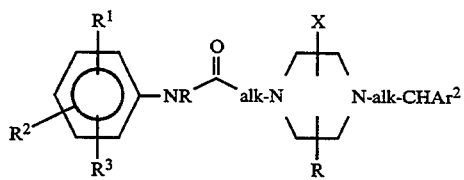

have been reported as anti-ischemic agents for myocardial tissue and for treating sleep disorders.

N-aryl-4-(4,4-diarylbutyl)-1-piperazinealkanamides optionally substituted in the piperazine ring are described as coronary vasodilators, local anesthetics, CNS-stimulants and anticarrageenin agents in U.S. Pat. No. 3,267,104 to Hermans and Schaper.

A structurally related series of compounds with different X substituents attached to the piperazine ring was disclosed as being useful in treating ischemia in cardiac tissue in U.S. Pat. No. 4,776,125 to Van Daele.

A series of piperazine derivatives including compounds of structure (3) have been claimed in U.S. Pat. No. 4,948,796 to Hiraiwa et al., as being useful for the protection of cerebral cells from ischemia.

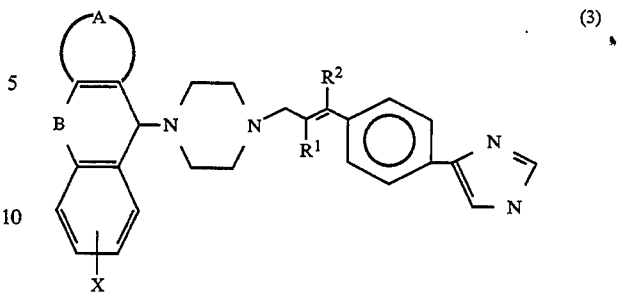

A method for treating neurodegenerative conditions by increasing extracellular concentrations of adenosine by use of, for example, adenosine transport inhibitors, was described by Marangos and Gruber in WO 91/04032.

There is nothing in any of the foregoing references, or in the general prior art, to suggest the novel antiischemic diphenyl-oxazoles, thiazoles and imidazoles of the present invention.

SUMMARY OF THE INVENTION

This invention is concerned with 1-piperazinyl-N-phenylacetamide derivatives of 4,5-diphenyl-oxazoles, thiazoles, and imidazoles which are novel adenosine transport inhibitors. These compound are useful in protecting CNS tissue, particularly neurons, against the effects of ischemia which can result from trauma or disorders such as stroke. The compounds are also useful in protection of cardiac tissue. The method involves administration of novel compounds of this invention to a mammal in need of such treatment.

DETAILED DESCRIPTION OF THE INVENTION

In its broadest aspect, the present invention comprises 1-piperazin-4-yl-N-phenylacetamide derivatives of 4,5-diphenyl-oxazoles, thiazoles, and imidazoles having anti-ischemic properties and which are structurally depicted by Formula I

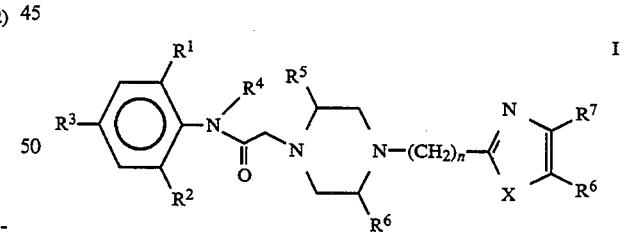

wherein $R^1$ and $R^2$ are independently selected from hydrogen, $C_{1-4}$ alkyl, $C_{1-4}$ alkoxy, halogen and trifluoromethyl;

$R^3$ is hydrogen, halogen, $C_{1-4}$ alkoxy or $-NR^9R^{10}$ with $R^9$ and $R^{10}$ being independently selected from hydrogen or $C_{1-4}$ alkyl; $C_1-C_5$ alkanoyl and

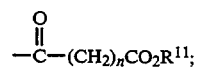

$R^4$ is hydrogen or $C_{1-4}$ alkyl;

$R^5$ and $R^6$ are independently selected from hydrogen, $-CO_2R^{11}$ with $R^{11}$ being $C_{1-4}$ alkyl, $-CONR^9R^{10}$ and oxo, or $R^5$ and $R^6$ can be taken together to form a methylene or ethylene bridge;

$R^7$ and $R^8$ are taken together as a butylene bridge or are each

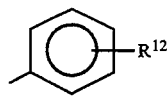

with $R^{12}$ being hydrogen, trifluoromethyl, halogen or $C_{1-4}$ alkyl;

n is zero or an integer from 1 to 4; and

X is S, O, or NH.

Pharmaceutically acceptable salt and/or solvates of the Formula I compounds also comprise the present invention which further includes stereoisomers such as enantiomers which can arise as a consequence of structural asymmetry in selected Formula I compounds. Separation of individual isomers is accomplished by application of various methods and procedures well known to practitioners in the art or by methods adapted for use with the instant series of compounds. An example of such a method is set forth in the preferred embodiment section of this specification.

Preferred compounds of Formula I comprise structures wherein $R^1$ and $R^2$ are methyl; $R^4$, $R^5$ and $R^6$ are hydrogen; and $R^7$ and $R^8$ are phenyl rings both substituted and unsubstituted. More preferred compounds are 2-aminocarbonyl-4-[(4,5-diphenyl-2-oxazolyl)methyl]-N-(4-amino-2,6-dichlorophenyl)-1-piperazineacetamide and N-(4-amino-2,6-dichlorophenyl)-4-[(4,5-diphenyloxazolyl)methyl]-1-piperazineacetamide.

For medicinal use, the pharmaceutically acceptable acid addition salts, those salts in which the anion does not contribute significantly to toxicity or pharmacological activity of the organic cation, are preferred. The acid addition salts are obtained either by reaction of an organic base of structure I with an organic or inorganic acid, preferably by contact in solution, or by any of the standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, pamoic acid, cyclamic acid, pivalic acid and the like: useful inorganic acids are hydrohalide acids such as HCl, HBr, HI; sulfuric acid; phosphoric acid and the like. The preferred solvate forms of Formula I compounds are hydrates.

The compounds of the present invention are useful pharmacologic agents with anti-ischemic properties. With adenosine potentiating properties, the compounds can be useful as neuroprotective, anticonvulsant and sleep improving agents. Representative compounds were selected and tested demonstrating their ability to potentiate pentobarbital-induced sleep time. Activity in this pharmacologic test indicates sedative potential for compounds as sleep agents.

Central nervous system tissue is particularly vulnerable to damage caused by ischemic conditions. Brain ischemia, or insufficient oxygen, may result from injury or disease and may last from only transient periods of time to periods of lengthy duration, as in stroke. In this regard, the compounds of Formula I are useful for treatment and prevention of injury to the brain and spinal cord and of edema due to head trauma, stroke, arrested breathing, cardiac arrest, Rey's syndrome, cerebral thrombosis, embolism, hemorrhage or tumors, encephalomyelitis, spinal cord injury, hydroencephalitis, and postoperative brain injury.

Numerous reports have suggested that adenosine plays a neuroprotective role in the central nervous system under conditions of anoxia, ischemia, and/or stroke. Therefore agents that increase adenosine levels in ischemic tissue should result in enhanced neuroprotection. From a pharmacologic standpoint, there are advantages to potentiating or maintaining adenosine levels by inhibiting the adenosine re-uptake transport system. Thus the anti-ischemic activity of the compounds of Formula I was initially demonstrated by effective inhibition of adenosine reuptake transport. This inhibition was measured by evaluating the compounds of Formula I for their ability to block the uptake of radiolabeled adenosine into rat cortical synaptosomes See: Bender, Wu and Phillis, The characterization of [$^3$H] adenosine uptake into rat cerebral cortical synaptosomes, 35 J. Neurochem. 629–640 (1980).

Selected compounds of Formula I, usually having $IC_{50}$ values of less than 10 μM in the adenosine reuptake transport inhibition assay, were also tested and gave positive results in in vivo stroke models such as protection of hippocampal tissue from ischemic cell loss resulting from bilateral carotid occlusion in a gerbil model and reduction of neocortical infarct volume after middle cerebral artery occlusion (MCAO) in the rat model.

Preferred compounds were also examined in pharmacologic tests indicating efficacy in cardiac ischemic states. In a Langendorff model of cardiac ischemia, isolated rat hearts were exposed to varying concentrations of the Formula I compound followed sequentially by 25 minutes of global ischemia and 30 minutes of reperfusion of the heart. Agents such as the Formula I compounds that increase the time required for the cardiac muscle tissue to contract are potential antiischemic drugs for treating ischemia of heart tissue.

The Formula I compounds were also tested in a canine model of cardiac infarct size reduction in which the agent was administered directly into the coronary artery of an anesthetized dog prior to a 90 minute coronary occlusion period followed by a five hour period of reperfusion. Infarct size in drug-treated animals was reduced compared to animals treated only with vehicle.

One aspect then of the present invention involves administration of a compound of Formula I or a pharmaceutically acceptable acid and/or solvate thereof, to a mammal suffering from ischemia or being susceptible to ischemia. In general the compound would be given in a dose range of from about 0.01 mg/kg to about 30 mg/kg body weight. The lower end of the dose range reflects parenteral administration and the upper end of the dose range reflects oral administration.

Although the dosage and dosage regimen of a Formula I compound must in each case be carefully adjusted, utilizing sound professional judgment and considering the age, weight and condition of the recipient, the route of administration and the nature and extent of the ischemia, generally, the daily dose for human use will be from about 0.5 g to about 10 g, preferably 1 to 5 g. In some instances, a sufficient therapeutic effect can be obtained at lower doses while in others, larger doses will be required. As is apparent to one skilled in clinical pharmacology, the amount of a Formula I compound comprising the daily dose may be given in a single or divided dose, taking into account those principles understood by the skilled practitioner and necessary for his practice of the art.

The term "systemic administration" as used herein refers to oral, sublingual, buccal, transnasal, transdermal, rectal, intramuscular, intravenous, intraventricular, intrathecal, and subcutaneous routes. In accordance with good clinical practice, it is preferred to administer the instant compounds at a concentration level which will produce effective beneficial effects without causing any harmful or untoward side effects.

Therapeutically, the instant compounds are generally given as pharmaceutical compositions comprised of an effective ischemia-protective amount of a Formula I compound or a pharmaceutically acceptable acid addition salt and/or hydrate thereof and a pharmaceutically acceptable carrier. Pharmaceutical compositions for effecting such treatment will contain a major or minor amount (e.g. from 95% to 0.5%) of at least one compound of the present invention in combination with a pharmaceutical carrier, the carrier comprising one or more solid, semi-solid, or liquid diluent, filler and formulation adjuvant which is non-toxic, inert and pharmaceutically acceptable. Such pharmaceutical compositions are preferably in dosage unit forms; i.e., physically discrete units having a predetermined amount of the drug corresponding to a fraction or multiple of the dose which is calculated to produce the desired therapeutic response. In usual practice, the dosage units contain 1, ½, ⅓, or less of a single dose. A single dose preferably contains an amount sufficient to produce the desired therapeutic effect upon administration at one application of one or more dosage units according to the predetermined dosage regimen, usually a whole, half, third, or less of the daily dosage administered once, twice, three, or more times a day. It is envisioned that other therapeutic agents can also be present in such a composition. Pharmaceutical compositions which provide from 0.1 to 1 g of the active ingredient per unit dose are preferred and are conventionally prepared as tablets, lozenges, capsules, powders, aqueous or oily suspensions, syrups, elixirs, and aqueous solutions. Preferred oral compositions are in the form of tablets, capsules, and may contain conventional excipients such as binding agents (e.g., syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from about 0.1% to 10% by weight of a Formula I compound or one of its salt forms in water or a vehicle consisting of a polyhydric aliphatic alcohol such as glycerine, propylene glycol, and the polyethylene glycols or mixtures thereof. The polyethylene glycols consist of a mixture of non-volatile, usually liquid, polyethylene glycols which are soluble in both water and organic liquids and which have molecular weights from about 200 to 1500.

When transnasal application is intended, the Formula I compound pharmaceutical composition is formulated in a pharmaceutical composition which enhances penetration of the nasal mucosa. Such formulations normally employ fatty acid salts of the Formula I base compound and their preparation and use would be known to one skilled in the pharmaceutical arts.

The general procedure for preparation of Formula I compounds is outlined in Scheme 1.

Scheme I
Synethesis of Formula I Products

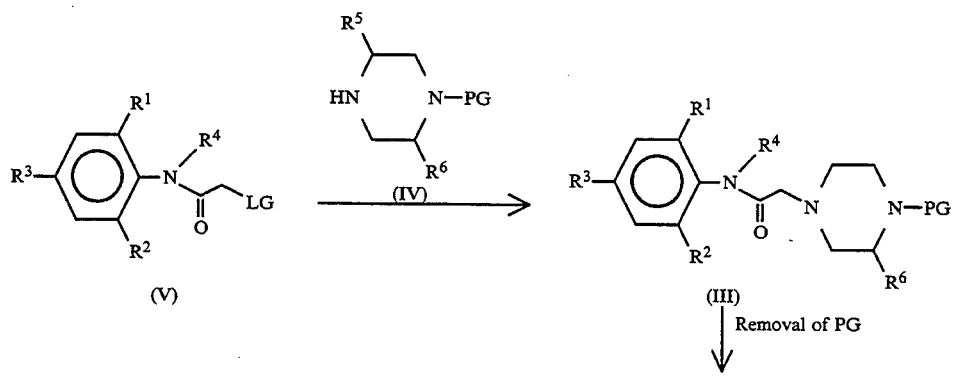

-continued
Scheme I
Synethesis of Formula I Products

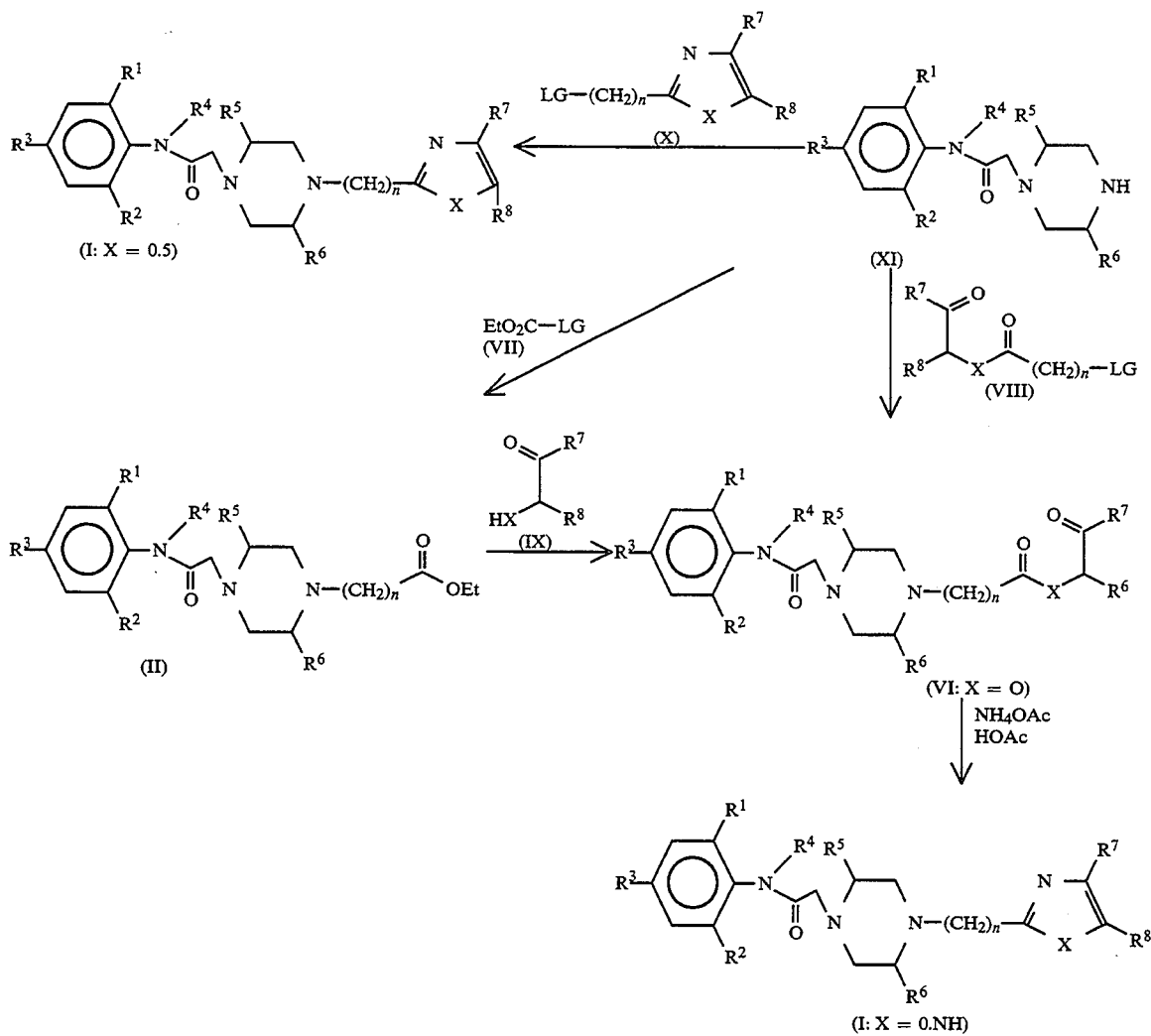

In Scheme 1; R¹-R⁸, X and n are as defined supra. LG is a synthetic organic leaving group of the type typically employed in synthetic organic chemistry. The most common leaving groups in such nucleophilic substitution-type reactions are the halides or sulfonic ester groups such as tosylate, brosylate, nosylate and mesylate. Synthetic organic leaving groups and their manipulations are well-known to one skilled in organic synthesis and have been fully described in the pertinent literature. See, e.g. March, *Advanced Organic Chemistry*, 2d ed.; McGraw-Hill: New York, pages 325-331. Carey and Sundberg, *Advanced Organic Chemistry A: Structure and Reactivity*, 3d ed. Plenum: New York, pages 270-292.

PG signifies a synthetic organic "protecting group" of the type generally used to "protect" a secondary amine functional group, e.g. an acyl-type group such as a carbobenzyloxy or t-butoxycarbonyl group or a trifluoroacetyl group or the like. Suitable "protecting" or "blocking" groups used in organic synthesis are also well known to the practitioner and are adequately described in the appropriate literature. See, e.g. Carey and Sundberg, *Advanced Organic Chemistry B: Reactions and Synthesis*, 3d ed.; Plenum: New York pages 677, 686-689.

The starting materials in Scheme 1 are N-phenylacetamide derivatives (V), such as a 2-halo-N-phenylacetamide; and "protected/blocked" piperazines (IV), such as 1-piperazine carboxaldehyde. These materials are either commercially available or can be readily prepared, e.g. bromoacetyl chloride and a substituted aniline are reacted to give V; a protecting group is attached to one nitrogen of the piperazine ring to provide IV. The product of the reaction of V and IV is an intermediate compound of Formula III which is "deprotected" by removal of PG, the protective or blocking group to give II which can be reacted with an appropriate diphenyl oxazole or thiazole (X) to give the desired Formula I product where X is S or O.

To prepare imidazole products, intermediate II can either be reacted with the keto-ester compound VIII to give VI or compound II can be reacted with the ester VII to give XI which is then treated with the keto alcohol IX to provide VI which can be converted to I wherein X is NH.

Reaction intermediates of Formula V can be obtained as shown in Scheme II.

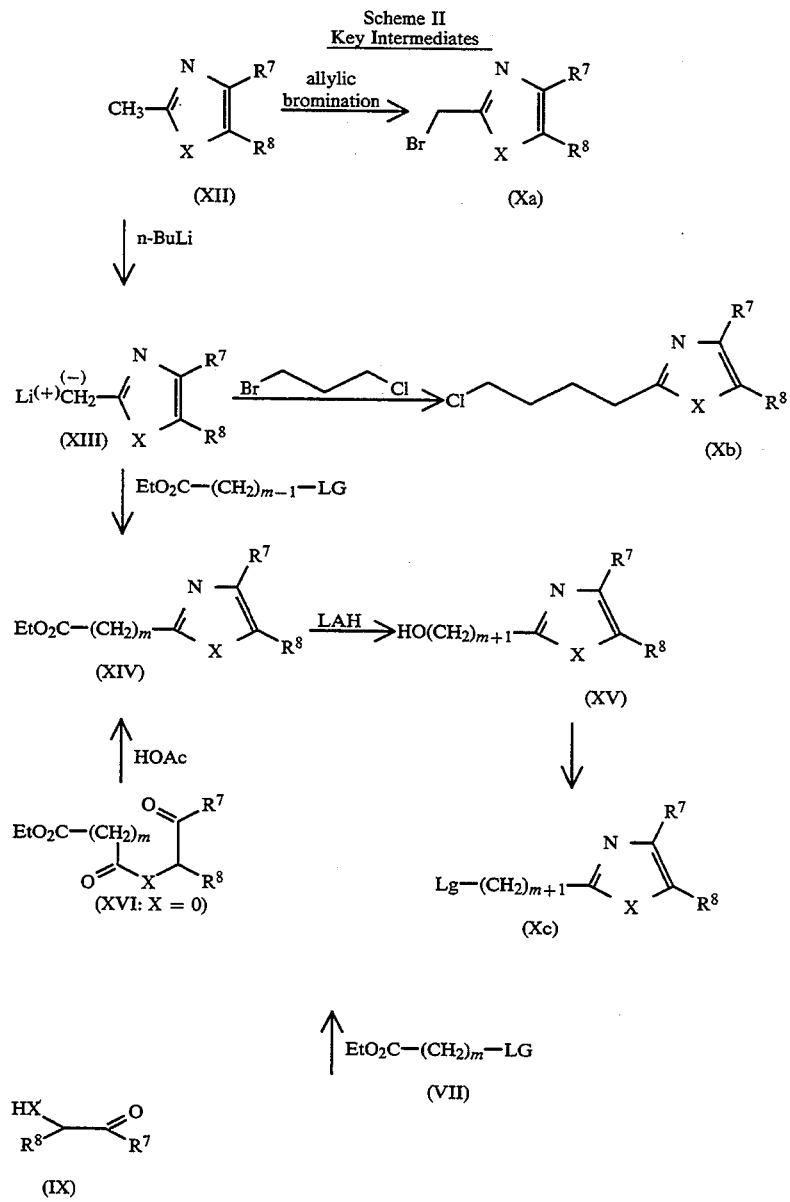

Scheme II
Key Intermediates

In Scheme II; $R^7$, $R^8$, LG and X are as previously defined. The symbol m can be an integer 1 to 3. Scheme II basically outlines the preparation of intermediates of Formula X with differing alkyl chain lengths for connection to piperazine intermediates (II) to provide certain Formula I products. Obvious variations to provide other products would be apparent to one skilled in synthetic organic chemistry, e.g. a thioketo alcohol could be used to prepare a thiazole intermediate of Formula XIV. Similarly, reaction of an α-bromo ketone with thioacetamide provides the thiazole intermediate XII.

As depicted in Scheme II, allylic bromination of 2-methyl-substituted intermediates of Formula XII yields Xa intermediates for use in Scheme I reactions. Lithiation of XII provides compound XIII which can either be alkylated with α, ω-disubstituted ethanes or propanes to yield $C_3$ or $C_4$ alkanyl chains (e.g. X6), or the XIII anion can be alkylated to provide a carbethoxy moiety at the terminus of the alkyl chain of XIV. This XIV compound can also be synthesized by reaction of XVII and XVIII to yield XVI which is aminated with ring-closure to provide XIV. Reduction of XIV with a hydride such as lithium aluminum hydride gives the corresponding intermediate alcohol XV which can be converted into Xc for use in Scheme I.

Compounds of Formula XII can be conveniently synthesized by acylation of XVIII with a propionyl halide or equivalent to form a propionate ester of XVIII. The ester is then aminated with ring-closure to give XII compounds.

Modification of these reaction schemes can be employed to produce Formula I compounds in somewhat different ways. For example, a reaction of compound V with a piperazine intermediate of Formula XXIV

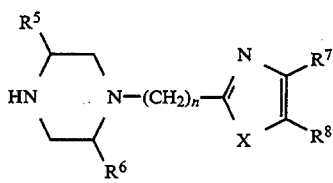

XXIV will directly yield a product of Formula I. Intermediates of Formula XXIV can be prepared utilizing intermediates of Formulas IV and X.

Description of Specific Embodiments

The compounds which constitute this invention and their methods of preparation will appear more fully from a consideration of the following examples which are given for the purpose of illustration only and are not to be construed as limiting the invention in sphere or scope. All temperatures are understood to be in °C. when not specified.

The nuclear magnetic resonance (NMR) spectral characteristics refer to chemical shifts ($\delta$) expressed as parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), singlet (s), multiplet (m), doublet (d), doublet of doublets (dd), quartet (q) or pentuplet (p). Abbreviations employed are DMSO-$d_6$ (deuterodi-methylsulfoxide). CDCl$_3$ (deuterochloroform), and are otherwise conventional. The elemental analyses are reported as percent by weight.

Synthesis of Intermediates

Several intermediate compounds as well as other conventional starting materials, e.g. VII, and IX; used in the preparation of final products I were generally commercially available. Representative syntheses of some of these compounds are provided hereinbelow nevertheless.

EXAMPLE 1

2-Methyl-4,5-bis[(trifluoromethyl)phenyl]oxazole (XII)

To a solution of 10 g (0.03 moles) of the intermediate of Formula IX, Example 6 in 100 ml of dichloromethane at 0°-5° C. was added 1.1 equivalent of (2.4 g) of pyridine, and catalytic amount of dimethylaminopyridine and 1.1 equivalent of acetyl chloride (2.3 g). The reaction mixture was stirred for 2 hours at room temperature. The solvent was evaporated and the residue was taken up in glacial acetic acid (100 ml) and refluxed in the presence of 5 equivalents of ammonium acetate (6.9 g) for a period of 1 to 2 hours and cooled to room temperature. Water was added (100 ml) and the product was isolated by extracting with ethyl acetate (3×100 ml), dried over Na$_2$SO$_4$ and concentrated to give 5.8 g of the desired product, m.p. 100°-102° C.

(C); $^1$H NMR (300 MHz, CDCl$_3$) $\delta$ 7.723 (m, 2H), 7.637 (m, 6H), 2.579 (s, 3H); $^{13}$C NMR (75 MHz, CDCl$_3$) $\delta$ 161.223, 128.013, 126.463, 125.735, 125.686, 125.612, 125.561, 13.842; IR (KBr) 3470, 3066, 1618, 1590, 1414, 1323, 1268, 1166, 1126, 1110, 1068, 1016, 966, 846, 674, 610 cm$^{-1}$; MS (DCI) m/e 372;

Anal. Calc'd for C$_{18}$H$_{11}$N$_1$O$_1$F$_6$: C, 58.23; H, 2.99; N, 3.77; Found: C, 57.98; H, 2.88; N, 3.68.

EXAMPLE 2

4,5-diphenyl-2-(4-chlorobutyl)oxazole (X)

To a solution of 2-methyl 4,5-diphenyloxazole (7.05 g, 0.3 mol) in 50 mL of dry THF at −78° C. was added 1.1 equivalent of n-BuLi or LDA and stirred for 30 min. To the dark red solution of the anion was added the alkylating reagent 3-chloro-1-bromopropane (1.1 equivalent) and the reaction mixture was allowed to warm to 0° C. over a period of 1 h. The reaction was worked up by adding NH$_4$Cl solution and extracting with ethyl acetate (50mL). Dried over Na$_2$SO$_4$, concentrated and purified by flash chromatography over silica gel using ether/hexane 1:4 as an eluant to give the Formula X compound 6.2 g (66%) as an oil. MS (DCI) m/z 311.

EXAMPLE 3

Ethyl 4-[[[(2,6-Dimethylphenyl)amino]carbonyl]methyl]-1-piperazineacetate (XI)

Ethyl bromoacetate (12.12 g, 0.073 mol) in dry acetonitrile (30 mL) was added dropwise to a mixture of N-(2,6-dimethylphenyl)-1-piperazineacetamide dihydrochloride hydrate (18.0 g, 0.073 mol) and potassium carbonate (18.0 g, 0.13 mol) in dry acetonitrile (200 mL). The mixture was stirred at room temperature for 16 h before it was filtered and evaporated. The residue was partitioned between ethyl acetate and water and the organic phase was separated, washed with brine dried and concentrated. There was isolated 21 g (86%) of the XI compound as a colorless oil which was used without further purification; $^1$H NMR (300 MHz, DMSO-$d_6$) $\delta$ 9.16 (s, 1H), 7.06 (s, 3H), 4.11 (q, J=3.6 Hz, 2H), 3.22 (s, 2H), 3.13 (s, 2H), 2.68 (br s, 8H), 2.14 (s, 6H), 1.19 (t, J=7.0 Hz, 3H); $^{13}$C NMR (75 MHz, DMSO-$d_6$) $\delta$ 171.65 (0), 169.63 (0), 166.02 (0), 136.72 (0), 136.67 (0), 129.36 (+), 128.09 (+), 63.07 (−), 61.54 (−), 60.24 (−), 54.67 (−), 53.59 (−), 19.7 (+), 15.88 (+); IR (KBr) 3242, 3020, 2988, 2964, 2936, 2914, 2878, 2824, 1744, 1662, 1530, 1478, 1466, 1444, 1428, 1390, 1380, 1306, 1278, 1224, 1198, 1166, 1136, 1042, 1020, 836, 762, 718 cm$^{-1}$; MS (DCI) m/e 334.

Anal. Calc'd for C$_{18}$H$_{27}$N$_3$O$_3$°1.5H$_2$O° 0.5C$_{16}$H$_{23}$N$_3$O$_3$: C, 60.86; H, 8.15; N, 12.28. Found: C, 60.66; H, 7.73; N, 12.48.

EXAMPLE 4

2-Oxo-1,2-di-(4-ethylphenyl)ethyl 4-[[[(2,6-dimethylphenyl)amino]carbonyl]-methyl]-1-piperazineacetate (VI)

1,3-Dicyclohexylcarbodiimide (DCC; 0.81 g, 3.92 mmol) was added in one portion to a rapidly-stirred mixture of 4-[[[(2,6-dimethylphenyl)amino]carbonyl]-methyl]-1-piperazineacetic acid (1.0 g, 3.27 mmol), 2-hydroxy-1,2-di-(4-ethylphenyl)ethanone (IX; 0.88 g, 3.27 mmol) and dimethylaminopyridine (DMAP: 40 mg) in anhydrous dimethylformamide (25 mL). After 2 hours at ambient temperature, an additional equivalent of DCC and DMAP were added. The mixture was stirred further for 22 hours at room temperature before it was heated to 70° C. for 6 hours. Upon cooling, the mixture was diluted with ethyl acetate, washed with saturated sodium bicarbonate solution and brine, dried and concentrated. Purification of the residue by flash chromatography on silica gel (gradient elution with 50% ethyl acetate in hexanes followed by ethyl acetate)

afforded 0.50 g of the benzoin ester product (VI) as an off-white solid. The ester was used in subsequent reactions without additional purification.

EXAMPLE 5

Bromoacetoxy-1,2-di-(4-ethylphenyl)ethanone (VIII)

A solution of bromoacetyl chloride (2.00 mL, 24.2 mmol) in anhydrous dichloromethane (20 mL) was added dropwise to a cold (0° C.) mixture of 2-hydroxy-1,2-di-(4-ethylphenyl)ethanone (IX; 6.5 g, 24.2 mmol) and N-methylmorpholine (NMM; 2.7 mL, 24.2 mmol) in anhydrous dichloromethane (180 mL). The mixture was stirred at 0° C. for 1 hour and at ambient temperature for 2 hours before additional 2-hydroxy-1,2-di-(4-ethylphenyl)ethanone (0.5 mL) and NMM (0.6 mL) were added to aid in completeion. After 1 hour, the mixture was washed with saturated sodium bicarbonate solution, 1$\underline{N}$ HCl and brine. Following drying and solvent evaporation, the residue was purified by flash chromatography on silica gel (gradient elution with 10% ethyl acetate in hexanes followed by 25% ethyl acetate in hexanes) and furnished 6.10 g (65%) of bromoacetoxy-1,2-di(4-ethylphenyl)ethanone as a pal-yellow oil which was used in subsequent reactions without further purification.

EXAMPLE 6

1,2-bis[4-(trifluoromethyl)phenyl]-2-hydroxyethanone (IX)

A mixture of 50 g (0.29 moles) of trifluoromethylbenzaldehyde and 0.7 g (0.05 equivalent) of sodium cyanide in 400 ml of 70% aqueous ethanol was heated to reflux for 20 hours. The reaction mixture was cooled, concentrated and the product was filtered to give crystals (42 g, 841) m.p. 77°-80° C.

$^1$H NMR (300 MHz, CDCl$_3$) δ 7.99 (d, J=8.13 Hz, 2H), 7.68 (d, J=8.26 Hz, 2H), 7.59 (d, J=8.14 Hz, 2H), 7.45 (d, J=8.15 Hz, 2H), 6.01 (s, 1H), 4.51 (s, 1H); $^{13}$C NMR (75 MHz, CDCl$_3$ δ 197.54, 141.80(0), 135.82, 129.26, 127.95, 126.19, 126.14, 126.09, 125.85, 125.81, 75.83, IR (KBr) 3436, 3074, 2940, 1696, 1680, 1618, 1514, 1420, 1332, 1250, 1174, 1132, 1114, 1098, 1070, 1018, 980, 878, 856, 830, 822, 700, 686, 626, 600 cm$^{-1}$; MS (DCI) m/e 349; Anal. Calc'd for C$_{16}$H$_{10}$O$_2$F$_6$: C, 55.18; H, 2.89; N, 0.00; Found: C, 55.12; H, 2.85; N, 0.14.

EXAMPLE 7

2-Bromo,chloro-N-(2,6-dimethylphenyl)acetamide (V)

A solution of bromoacetyl chloride (20.0 mL, 0.234 mol) in anhydrous dichloromethane (20 mL) was added dropwise to a cold (0° C.) mixture of 2,6-dimethylaniline (29.5 mL, 0.234 mol) and N-methylmorpholine (28.0 mL, 0.254 mol) in anhydrous dichloromethane (500 mL). The mixture was stirred at 0° C. for 1 h and at ambient temperature for 2 h before it was washed with 1$\underline{N}$ NaOH, 1$\underline{N}$ HCl and brine. Following drying and solvent evaporation, the residue was triturated with hot ether/ethyl acetate to yield after suction-filtration 46.75 g (83%) of the Formula V compound(s) as an off-white solid, m.p. 148°-149° C.; $^1$H NMR (300 MHz, CDCl$_3$) δ 8.28 (br s, 1H), 7.08-6.97 (m, 3H), 4.14 (s, 0.5H), 3.93 (s, 1.5H), 2.16 and 2.15 (2s, 6H); $^{13}$C NMR (75 MHz, CDCl$_3$) ppm 164.96, 135.63, 133.41, 128.44, 128.39, 127.78, 42.92, 29.04, 18.41; IR (KBr) 3440, 3212, 3042, 2974, 1644, 1534, 1476, 1308, 1218, 1120, 762 cm$^{-1}$; MS (DCI) m/z 242.

Anal. Calc'd for 0.75C$_{10}$H$_{12}$BrNO°0.25C$_{10}$H$_{12}$ClNO: C, 51.02; H, 5.19; N, 5.92. Found: C, 51.27; H, 5.10; N, 6.06.

EXAMPLE 8

(4-Nitro-2,6-dichlorophenyl)-2-bromoacetamide (V)

A mixture of 4-nitro-2,6-dichloroaniline (17 g, 82 mmol), bromoacetyl chloride (25 mL, 304 mmol), water (0.6 mL), H$_2$SO$_4$ (3.0 g), and trifluoroacetic acid (150 mL) in methylene chloride (150 mL) was stirred at room temperature for 5 days. The resulting mixture was poured into 500 mL of hot water and stirred for 45 minutes. A yellow precipitate (23.32 g) was collected by filtration. The precipitate was washed with water and methanol, and then triturated in methylene chloride-ether to yield an off-white solid (11.56 g, 43% yield): m.p. 195°-197° C.; $^1$H NMR (300 MHz, CDCl$_3$) δ 4.14 (s, 2H), 8.12 (broad s, 1H), 8.33 (s, 2H).

EXAMPLE 9

N-(tert-butoxycarbonyl)-3-aminocarbonylpiperazine (IV)

To a solution of 2-aminocarbonylpiperazine (9.83 g, 76.2 mmol) and triethylamine (10.7 mL, 76 mmol) in 200 mL of DMF at −20° C. was added di-tert-butyl dicarbonate (16.6 g, 76.2 mmol). This was stirred for 2 hours, and warmed to room temperature. Solvent was then removed in vacuo to yield a yellowish-white solid (19.8 g). This was recrystallized in methylene chloride-ether to yield IV as a white solid (15.46 g, 89% yield): m.p. 103°-106° C.; $^1$H NMR (300 MHz, CDCl$_3$) δ 1.46 (s, 9H), 1.85-2.00 (m, 1H), 2.73-2.82 (m, 1H), 2.87-3.18 (m, 2H), 3.32-3.38 (m, 1H), 3.70-3.85 (m, 1H), 4.01-4.10 (m, 1H), 5.54 (broad s, 1H), 6.70 (broad s, 1H).

EXAMPLE 10

N-(2,6-Dimethylphenyl)-4-formyl-1-piperazineacetamide (III)

A mixture of 2-bromo,chloro-N-(2,6-dimethylphenyl)acetamide (V: 24.2 g, 0.10 mol), anhydrous sodium carbonate (15.9 g, 0.15 mol), sodium iodide (0.10 g) and 1-piperazine carboxaldehyde (IV: 10.3 mL, 0.10 mol) in anhydrous dimethylformamide (200 mL) was heated to 85° C. for 6 h before it was cooled, suction-filtered and concentrated down in vacuo. The residue was then dissolved in a minimal amount of hot 5% methanol in ethyl acetate. After 2 h at ambient temperature, the mixture was suction-filtered and the filtrate was concentrated down once again to yield a grey-colored solid which was recrystallized from ethyl acetate. There the Formula III compound was isolated 17.95 g (65%) as a white solid, m.p. 139°-140° C.; $^1$H NMR (300 MHz, CDCl$_3$) δ 8.50 (br s, 1H), 7.99 (s, 1H), 7.25-7.03 (m, 3H), 3.59-5.56 (m, 2H), 3.42-3.39 (m, 2H), 3.17 (s, 2H), 2.66-2.59 (m, 4H), 2.19 (s, 6H); $^{13}$C NMR (75 MHz, CDCl$_3$) ppm 167.96, 160.96, 135.18, 133.67, 128.53, 127.55, 61.89, 54.28, 53.21, 45.69, 40.07, 18.83; IR (KBr) 3432, 3274, 2958, 1672, 1506, 1446, 1436, 1148, 1020, 1008, 788 cm$^{-1}$; MS m/z calc'd for C$_{15}$H$_{22}$N$_3$O$_2$ 276.1712, found 276.1709.

Anal. Calc'd for C$_{15}$H$_{21}$N$_3$O$_2$: C, 65.43; H, 7.69; N, 15.26. Found: C, 65.42; H, 7.76; N, 15.32.

EXAMPLE 11

2-(aminocarbonyl)-N-(4-nitro-2,6-dichlorophenyl)-4-(tert-but oxycarbonyl)-1-piperazineacetamide (III)

A mixture of (4-nitro-2,6-dichlorophenyl)-2-bromoacetamide (2.57 g, 7.84 mmol), 2-aminocarbonyl-4-tert-butoxycarbonylpiperazine (1.80 g, 7.86 mmol), and $K_2CO_3$ (4.35 g) in 50 mL of DMF was stirred at room temperature for 24 hours. The resulting mixture was partitioned between ethyl actate and water, and the aqueous extract vigorously re-extracted with ethyl acetate. After removal of solvent in vacuo, the combined ethyl acetate extracts yielded 2.59 g of residue. This was recrystallized in methylene chloride-hexane to yield III as a white solid (1.67 g, 45% yield): m.p.>123° C. (dec.); $^1$H NMR (300 MHz, $CDCl_3$) δ 1.45 (s, 9H), 2.47–2.55 (m, 1H), 3.05–3.10 (m, 1H), 3.15–3.35 (m, 4H), 3.50–3.56 (d, 1H), 3.83 (broad s, 1H), 4.00–4.04 (m, 1H), 5.59 (broad s, 1H), 6.12 (broad s, 1H), 8.24 (s, 2H), 9.40 (broad s, 1H); MS (FAB) m/z 476 (M+).

EXAMPLE 12

2-(aminocarbonyl)-N-(4-amino-2,6-dichlorophenyl)-4-(tert-butoxycarbonyl)-1-piperazineacetamide (III)

A solution of 2-(aminocarbonyl)-N-(4-nitro-2,6-dichlorophenyl)-4-(tert-butoxycarbonyl)-1-piperazineacetamide (1.0 g, 2.1 mmol) in 30 mL of methanol containing methanolic 4% thiophene (0.25 mL) and 5% platinum on charcoal catalyst (450 mg) was hydrogenated using a Parr apparatus at 50° C. and 25 psi for 30 minutes. After cooling and removal of catalyst by filtration, the solvent was removed from the filtrate in vacuo to yield III as an amorphous solid (0.88 g, 94% yield).

EXAMPLE 13

N-(4-nitro-2,6-dichlorophenyl)-4-formyl-1-piperazineacetamide (III)

A mixture of N-formylpiperazine (0.41 mL, 4.0 mmol), (4-nitro-2,6-dichlorophenyl)-2-bromoacetamide (1.31 g, 4.0 mmol), and $K_2CO_3$ (2.2 g) in 20 mL of DMF was stirred at room temperature for 15 minutes. The mixture was then partitioned between ethyl acetate and water, the aqueous extracts were diluted with brine, and then exhaustively extracted with ethyl acetate. Solvent was removed in vacuo from the combined ethyl acetate extracts to yield the III product as a residue (1.79 g): $^1$H NMR (300 MHz, $CDCl_3$) δ 2.73–2.78 (m, 2H), 2.85–2.97 (m, 4H), 3.34 (s, 2H), 3.51–3.56 (m, 1H), 3.68–3.72 (m, 1H), 8.30 (s, 2H), 9.14 (broad s, 1H).

EXAMPLE 14

N-(4-amino-2,6-dichlorophenyl)-4-formyl-1-piperazineacetamide (III)

A mixture of N-(4-nitro-2,6-dichlorophenyl)-4-formyl-1-piperazineacetamide (1.79 g crude) was suspended in methanol (50 mL) containing 4% methanolic thiophene (0.5 mL) and 5% platinum on charcoal catalyst (900 mg). This was hydrogenated using a Parr apparatus for 30 minutes at 50° C. and 26 psi. After filtration and the removal of solvent in vacuo, the filtrate yielded 1.38 g of crude residue. This was subjected to flash chromatography on deactivated silica gel (from a slurry of 300 g of silica gel in methylene chloride containing 3.4 mL of conc. $NH_4OH$). The product was eluted with $CH_2Cl_2$:MeOH:$NH_4OH$ 98.8:1.0:0.2 yielding 590 mg of III an off-white solid. This was triturated in methylene chloride-ether to yield a white solid (520 mg, 39% yield).: m.p.>220° C. (dec.).

EXAMPLE 15

N-(2,6-Dimethylphenyl)-1-piperazineacetamide Dihydrochloride Hydrate (II)

N-(2,6-dimethylphenyl)-4-formyl-1-piperazineacetamide (17.70 g, 64.0 mmol) was dissolved in a mixture of methanol (500 mL) and 1N HCl (130 mL) under nitrogen. The mixture was refluxed for 7 h before it was cooled, concentrated and partitioned between ethyl acetate and water. The aqueous phase was then separated away from the organic phase and evaporated down to dryness. There was isolated 21.00 g (98%) of the title compound as a white solid, m.p. 185°–195° C. (sealed tube); $^1$H NMR (300 MHz, $D_2O$) δ 7.11–7.01 (m, 3H), 4.31 (s, 2H), 3.65–3.62 (m, 4H), 3.56–3.50 (m, 4H), 2.04 (s, 6H); $^{13}$C NMR (75 MHz, $D_2O$) ppm 168.55, 140.74, 136.95, 133.37, 133.19, 61.89, 54.16, 45.56, 22.24; IR (KBr) 3440, 2958, 1690, 1532, 1472, 1442, 1386, 1308, 1240, 964, 770 cm$^{-1}$; MS m/z calc'd for $C_{14}H_{22}N_3O$ 248.1763, found 248.1763.

Anal. Calc'd for $C_{14}H_{21}N_3O$·2.0HCl°0.8H$_2$O: C, 50.20; H, 7.41; N, 12.55; H$_2$O, 4.38. Found: C, 50.19; H, 7.26; N, 12.22; H$_2$O, 2.60.

EXAMPLE 16

Ethyl 4-[[[(2,6-Dimethylphenyl)amino]carbonyl]methyl]-2-piperazinecarboxylate Dihydrochloride Hydrate (II)

A mixture of 2-bromo,chloro-N-(2,6-dimethylphenyl)acetamide (15.39 g, 0.063 mol), anhydrous sodium carbonate (6.709 g, 0.063 mol), sodium iodide (0.95 g) and ethyl 2-piperazineacetate (10.09 g, 0.063 mol) in anhydrous dimethylformamide (200 mL) was heated to 100° C. for 6 h before it was cooled and concentrated down in vacuo. The residue was then partitioned between ethyl acetate and water and the organic phase was separated, washed with brine, dried and concentrated. Purification of the residue by flash chromatography on silica gel (gradient elution with absolute ethyl acetate followed by 10% methanol in ethyl acetate) gave 11.60 g (57%) of the Formula II compound as a brown oil which was sufficiently pure to be used directly and 5.15 g (16%) of ethyl 1,4-[bis[[(2,6-dimethylphenyl)amino]carbonyl]methyl]-2-piperazine carboxylate as a by-product. A small portion of II compound was converted to its dihydrochloride salt with ethereal hydrochloride for characterization purposes. There was isolated an off-white solid, m.p. 149°–159° C. (185° C. decomp. pt., sealed tube); $^1$H NMR (300 MHz, DMSO-$d_6$) d 10.15 (br m, 1H), 9.77 (s, 1H), 7.06 (s, 3H), 4.54–4.51 (m, 1H), 4.21 (q, J=7.1 Hz, 2H), 3.70 (m, 2H), 3.56–3.52 (m, 1H), 3.40–3.02 (series of m, 5H), 2.13 (s, 6H), 1.21 (t, J=7.1 Hz, 3H); $^{13}$C NMR (75 MHz, DMSO-$d_6$) ppm 166.15, 165.67, 135.29, 134.61, 127.78, 126.76, 62.40, 58.51, 53.80, 50.42, 48.30, 41.39, 18.32, 13.92; IR (KBr) 3432, 2982, 2924, 2828, 2732, 2476, 1748, 1668, 1506, 1472, 1444, 1376, 1296, 1274, 1220, 1098, 774 cm$^{-1}$; MS m/z calc'd for $C_{17}H_{26}N_3O_3$ 320.1974, found 320.1982.

Anal. Calc'd for $C_{17}H_{25}N_3O_3$·2.0HCl°0.1H$_2$O°0.2Et$_2$O: C, 52.28; H, 7.20; N, 10.28; H$_2$O, 0.44. Found: C, 52.46; H, 7.58; N, 10.34; H$_2$O, 5.52.

same procedure used as for 2-piperazinecarboxamide Felder, E.; Maffei, S.; Pietra, S.; Pitre, D. *Helv. Chim. Acta.* 1960, 43, 888.

EXAMPLE 17

3-Aminocarbonyl-N-(2,6-dimethylphenyl)-1-piperazineacetamide Dihydrochloride Hydrate (II)

A mixture of 2-bromo,chloro-N-(2,6-dimethylphenyl)acetamide (9.37 g, 38.71 mmol), anhydrous sodium carbonate (4.10 g, 38.71 mmol), sodium iodide (0.58 g) and 2-piperazinecarboxamide (5.0 g, 38.71 mmol) in anhydrous dimethylformamide (200 mL) was heated to 100° C. for 6 h before it was cooled and concentrated down in vacuo. The residue was then partitioned between ethyl acetate and water and the organic phase was separated, washed with brine, dried and concentrated. Purification of the residue by flash chromatography on silica gel (gradient elution with absolute ethyl acetate followed by 10% methanol in ethyl acetate) gave 4.25 g (38%) of the Formula II compound as an off-white foam and 3.15 g (18%) of 2-(aminocarbonyl)-N,N'-bis(2,6-dimethylphenyl)-1,4-piperazinediacetamide as a by-product. A small portion of the title compound was converted to its dihydrochloride salt with methanolic hydrochloride for characterization purposes. There was isolated an off-white solid, m.p. 185°–222° C. (dec., sealed tube); $^1$H NMR (300 MHz, DMSO-$d_6$) δ 10.17 (s, 1H), 10.80–10.20 and 9.80–9.60 (2 br s, 1H), 8.38 (s, 1H), 7.88 (s, 1H), 7.08 (s, 3H), 4.29–4.22 (m, 1H), 4.16 (br s, 2H), 3.93–3.90 (m, 1H), 3.58–3.55 (m, 1H), 3.44–3.31 (m, 4H), 2.17 (s, 6H); $^{13}$C NMR (75 MHz, DMSO-$d_6$) ppm 167.75, 165.24, 136.83, 135.78, 129.47, 128.57, 58.49, 55.13, 52.22, 49.60, 20.01; IR (KBr) 3406, 3168, 3016, 2698, 2466, 1694, 1538, 1472, 1442, 1398, 774 cm$^{-1}$; MS m/z calc'd for $C_{15}H_{23}N_4O_2$ 291.1821, found 291.1815.

Anal. Calc'd for $C_{15}H_{22}N_4O_2$·2.0HCl·0°2.6H$_2$O: C, 43.93; H, 7.18; N, 13.66; H$_2$O, 11.42. Found: C, 42.43; H, 6.15; N, 12.82; H$_2$O, 10.6.

Felder, E.; Maffei, S.; Pietra, S.; Pitre, D. *Helv. Chim. Acta.* 1960, 43, 888.

EXAMPLE 18

2-(aminocarbonyl)-N-(4-amino-2,6-dichlorophenyl)-1-piperazineacetamide trifluoroacetate (II)

A solution of 2-(aminocarbonyl)-N-(4-amino-2,6-dichlorophenyl)-4-(tert-butoxycarbonyl)-1-piperazineacetamide (0.88 g, 2.0 mmol) in trifluoroacetic acid (10 mL) was stirred at room temperature for 20 minutes, then the solvent was removed in vacuo to yield a viscous oil (2.34 g, 100% yield) as a (tri)-trifluoroacetate salt containing some residual trifluoroacetic acid.

EXAMPLE 19

N-(4-amino-2,6-dichlorophenyl)-1-piperazineacetamide (II)

A solution of N-(4-amino-2,6-dichlorophenyl)-4-formyl-1-piperazineacetamide (470 mg, 1.42 mmol) in 1N HCl (20 mL) was refluxed for 45 minutes, and the aqueous HCl removed azeotropically with n-propanol. The residue (610 mg) was recrystallized in methanolmethylene chloride to yield 505 mg of an off-white solid. This material was dissolved in methanol and basified with conc. NH$_4$OH. After the removal of solvent in vacuo, the residue was dissolved in methanol and filtered. The filtrate yielded, after solvent removal, II as an amorphous residue (370 mg, 86% yield).

EXAMPLE 20

N-(4,5-diphenyloxazolyl)methyl piperazine (XXIV)

A mixture of 4,5-diphenyl-2-bromomethyloxazole (X; 20 g, 0.063 moles) and excess piperazine (10 mol equivalent) in 400 ml of absolute ethanol was stirred overnight at room temperature. The reaction mixture was evaporated and the residue was taken up in 4X200 ml of methylene chloride and washed several times with water and brine. The organic layer was dried over Na$_2$SO$_4$, evaporated and the product was obtained as a yellow solid (19.8 g, 95%) after passing through a silica gel column and eluting with a mixture of methanol/chloroform (1:9). This procedure is amenable for large scale synthesis. MS (DCl) MH+ 320.

Synthesis of Formula I Products

EXAMPLE 21

3-Aminocarbonyl-4-[(4,5-diphenyl-2-oxazolyl)methyl]-N-(2,6-dimethylphenyl)-1-piperazineacetamide Dihydrochloride Hydrate (I)

A mixture of 3-aminocarbonyl-N-(2,6-dimethylphenyl)-1-piperazineacetamide (0.50 g, 1.72 mmol), anhydrous sodium carbonate (0.18 g, 1.72 mmol), sodium iodide (26 mg) and 2-bromomethyl-4,5-diphenyloxazole (0.54 g, 1.72 mmol) in anhydrous dimethylformamide (30 mL) was heated to 100° C. for 3 h before it was cooled and concentrated down in vacuo. The residue was then taken up in ethyl acetate and washed with saturated sodium bicarbonate solution and brine. Following drying and solvent evaporation, the residue was purified by flash chromatography on silica gel (gradient elution with absolute ethyl acetate followed by 10% methanol in ethyl acetate) and afforded 0.62 g (55%) of the Formula I compound as a pinkish-tan solid after salt formation with ethereal hydrogen chloride, m.p. 138°–176° C. (185° C. decomp. pt., sealed tube); $^1$H NMR (300 MHz, DMSO-$d_6$) δ 10.37 (s, 1H), 8.01 (br s, 1H), 7.76 (br s, 1H), 7.64–7.59 (m, 4H), 7.51–7.36 (m, 6H), 7.10 (s, 3H), 5.80–4.40 (br s, 3H), 4.31 (s, 2H), 4.05 (m, 2H), 3.78 (m, 1H), 3.65–3.62 (m, 1H), 3.51–3.27 (series of m, 4H), 3.18–3.08 (m, 1H), 2.18 (s, 6H); $^{13}$C NMR (75 MHz, DMSO-$d_6$) ppm 171.38, 164.43, 160.35, 147.31, 136.77, 136.29, 135.57, 133.46, 130.88, 130.72, 130.44, 130.09, 129.91, 129.52, 129.19, 128.66, 128.35, 66.65, 58.03, 54.29, 52.64, 51.47, 19.92, 16.91; IR (KBr) 3402, 3176, 3022, 2558, 1694, 1602, 1540, 1508, 1474, 1444, 1410, 1378, 1224, 1158, 840, 774, 582 cm$^{-1}$; MS m/z calc'd for $C_{31}H_{34}N_5O_3$ 524.2662, found 524.2645.

Anal. Calc'd for $C_{31}H_{33}N_5O_3$·2.0HCl·0.35Et$_2$O·1.8-H$_2$O: C, 59.42; H, 6.48; N, 10.69; H$_2$O, 4.95. Found: C, 59.74; H, 5.94; N, 10.89; H$_2$O, 5.5.

EXAMPLE 22

N-(2,6-Dimethylphenyl)-4-[4,5-diphenyl-2-oxazolyl]-1-piperazineacetamide Dihydrochloride (I)

A mixture of 2-chloro-4,5-diphenyloxazole (1.52 g, 5.97 mmol), anhydrous sodium carbonate (1.89 g, 17.91 mmol), and N-(2,6-dimethylphenyl)-1-piperazineacetamide dihydrochloride hydrate (2.0 g, 5.97 mmol) in xylenes/anhydrous dimethylformamide (25 mL/10 mL) was heated to reflux under nitrogen for 6 h before it was cooled and concentrated down in vacuo. The residue was then taken up in ethyl acetate and washed with brine. Following drying and solvent evaporation, the residue was purified by flash chromatography on silica gel (elution with 50% ethyl acetate in hexanes) and afforded a slightly impure white solid which was recrystallized from ethyl acetate. Salt formation with methanolic hydrogen chloride gave 1.27 g (40%) of the Formula I compound as a white solid, m.p. 190°–209° C. (dec., sealed tube); $^1$H NMR (300 MHz, DMSO-d$_6$) d 10.94 (m, 0.5H), 10.46 (s, 1H), 7.58–7.54 (m, 2H), 7.50–7.45 (m, 2H), 7.43–7.28 (m, 6H), 7.09 (s, 3H), 4.41 (s, 2H), 4.18 (m, 2H), 3.63–3.50 (2 m, 6H), 2.18 (s, 6H); $^{13}$C NMR (75 MHz, DMSO-d$_6$) ppm 162.62, 158.63, 139.57, 135.08, 134.40, 133.83, 132.17, 128.85, 128.62, 128.30, 127.92, 127.83, 127.51, 126.98, 125.42, 56.11, 50.55, 42.44, 18.23; IR (KBr) 3422, 3182, 3022, 2562, 1690, 1602, 1592, 1540, 1474, 1444, 1404, 1348, 1288, 1238, 960, 766, 694 cm$^{-1}$; MS (DCI) m/z 467.

Anal. Calc'd for $C_{29}H_{30}N_4O_2 \cdot 1.7HCl \cdot 0.3H_2O$: C, 65.23; H, 6.10; N, 10.49; Cl, 11.29; H$_2$O, 1.01; Found: C, 65.28; H, 6.10; N, 10.34; Cl, 0.00; H$_2$O, 1.24.

Gompper, R.; Effenberger, F. *Chem. Ber.* 1959, 92, 1928.

EXAMPLE 23

N-(2,6-Dimethylphenyl)-4-[2-(4,5-diphenyl-2-oxazolyl)ethyl]-1-piperazineacetamide Dihydrochloride Hydrate (I)

To a cold (−10° C.) solution of ethyl 4,5-diphenyl-2-oxazoleacetate (CA:956963, Oct. 29, 1974), (3.0 g, 9.76 mmol) in anhydrous tetrahydrofuran (150 mL) was added lithium aluminium hydride (0.37 g, 9.76 mmol). After 0.5 h, an additional 0.5 eq of LAH (0.37 g) was added and the mixture was allowed to stir at −10° C. for an additional 3 h before it was quenched with 1N HCl. The mixture was then diluted with ethyl acetate and washed with 1N HCl, saturated sodium bicarbonate solution and brine. Following drying and solvent evaporation, the residue was taken up in dry dichloromethane (10 mL) and treated with triethylamine (0.47 mL, 3.39 mmol) and methanesulfonyl chloride (0.26 mL, 3.39 mmol) at 0° C. After 0.5 h at 0° C., the mixture was diluted with dichloromethane and washed with saturated sodium bicarbonate solution and brine prior to drying and solvent concentration. The mesylate was then treated with N-(2,6-dimethylphenyl)-1-piperazineacetamide dihydrochloride hydrate (1.14 g, 3.39 mmol) under the standard alkylating conditions given supra. There was isolated 0.24 g (12%), of the Formula I compound as a pale-yellow solid, m.p. 193°–203° C. (sealed tube); $^1$H NMR (300 MHz, D$_2$O/DMSO-d$_6$) δ 10.16 (br s, 1H), 7.55–7.50 (m, 4H), 7.45–7.30 (m, 6H), 7.05 (s, 3H), 4.26 (br s, 2H), 3.68–3.43 (2 m, 10H), 2.13 (s, 6H); $^{13}$C NMR (75 MHz, D$_2$O/DMSO-d$_6$) ppm 167.51, 160.63, 147.14, 136.72, 135.61, 134.35, 132.36, 130.78, 130.40, 130.29, 129.38, 128.97, 128.91, 127.74, 59.11, 53.83, 51.33, 50.67, 24.04, 19.01; IR (KBr) 3422, 3178, 2974, 2394, 1684, 1538, 1502, 1474, 1444, 1378, 1286, 962, 766, 696 cm$^{-1}$; MS (DCI) m/z 495.

Anal. Calc'd for $C_{31}H_{34}N_4O_2 \cdot 2.0HCl \cdot 1.7H_2O \cdot 0.1Et_2O$: C, 62.28; H, 6.73; N, 9.25; H$_2$O, 5.06. Found: C, 62.51; H, 6.48; N, 8.99; H$_2$O, 5.12.

EXAMPLE 24

4-[[4,5-Bis(4-ethylphenyl)-2-imidazolyl]methyl]-N-(2,6-dimethylphenyl)-1-piperazineacetamide Trihydrochloride Hydrate and 4-[[4,5-Bis(4-ethylphenyl)-2-oxazolyl]methyl]-N-(2,6-dimethyl phenyl)-1-piperazineacetamide Dihydrochloride Hydrate (Method A):

1,3-Dicyclohexylcarbodiimide (DCC; 0.81 g, 3.92 mmol) was added in one portion to a rapidly-stirred mixture of 4-[[[(2,6-dimethylphenyl)amino]carbonyl]methyl]-1-piperazineacetic acid (1.0 g, 3.27 mmol), 2-hydroxy-1,2-di-(4-ethylphenyl)ethanone (IX; 0.88 g, 3.27 mmol) and dimethylaminopyridine (DMAP: 40 mg) in anhydrous dimethyl-formamide (25 mL). After 2 h at ambient temperature, an additional equivalent of DCC and DMAP were added. The mixture was stirred further for 22 h at room temperature before it was heated to 70° C. for 6 h. Upon cooling, the mixture was diluted with ethyl acetate, washed with saturated sodium bicarbonate solution and brine, dried and concentrated. Purification of the residue by flash chromatography on silica gel (gradient elution with 50% ethyl acetate in hexanes followed by ethyl acetate) afforded 0.50 g of the benzoin ester (VI) as an off-white solid. The ester was taken up in glacial acetic acid (15 mL) and solid ammonium acetate (0.17 g) was added. After 0.5 h at reflux, additional ammonium acetate (0.17 g) was added and the mixture was heated further for 2 h before it was cooled and concentrated down in vacuo. The residue was purified by flash chromatography on silica gel (gradient elution with absolute ethyl acetate followed by 10% methanol in ethyl acetate) and furnished after acidification with HCl in methanol 0.14 g (3.8%, two steps) of the oxazole product as a tan solid and 0.15 g (3.9%, two steps) of the imidazole product as an off-white solid.

For the Formula I oxazole: m.p. 223°–227° C. (dec., sealed tube); $^1$H NMR (300 MHz, DMSO-d$_6$) δ 10.10 (s, 1H), 7.54–7.50 (m, 4H), 7.34–7.26 (m, 4H), 7.10 (s, 3H), 4.25 (br s, 2H), 4.13 (br s, 2H), 3.60–2.8 (br m, 7H), 2.69–2.60 (m, 4H), 2.16 (s, 6H), 1.21 (t, J=7.6 Hz, 6H); $^{13}$C NMR (75 MHz, DMSO-d$_6$) ppm 164.57, 157.96, 147.63, 146.83, 145.76, 136.79, 136.03, 135.54, 130.70, 130.11, 129.82, 129.53, 129.07, 128.68, 128.38, 127.24, 57.81, 53.14, 51.98, 49.95, 29.70, 29.66, 19.91, 17.09, 17.00; IR (KBr) 3430, 2964, 2930, 2872, 1684, 1538, 1522, 1444, 1060, 966, 836 cm$^{-1}$; MS m/z calc'd for $C_{34}H_{41}N_4O_2$ 537.3229, found 537.3223.

For the Formula I imidazole: m.p. 208°–215° C. (dec., sealed tube); $^1$H NMR (300 MHz, DMSO-d$_6$) δ 10.28 (s, 1H), 7.44 (d, J=8.2 Hz, 4H), 7.32 (d, J=8.3 Hz, 4H), 7.10 (s, 3H), 4.32 (s, 2H), 4.14 (s, 2H), 3.85 (br s, 12H), 3.53 (br s, 2H), 3.37 (br s, 2H), 3.15 (br s, 2H), 2.65 (q, J=7.6 Hz, 4H), 2.17 (s, 6H), 1.20 (t, J=7.5 Hz, 6H); $^{13}$C NMR (75 MHz, DMSO-d$_6$) ppm 164.46, 146.98, 136.74, 135.48, 130.16, 129.90, 129.57, 128.74, 126.51, 57.58, 53.04, 51.64, 50.36, 29.64, 19.89, 17.01; IR (KBr) 3422, 2964, 2932, 2544, 1688, 1640, 1532, 1444, 1416, 1384, 836, 770 cm$^{-1}$; MS m/z calc'd for $C_{34}H_{42}N_5O$ 536.3389, found 536.3391.

EXAMPLE 25

4-[[4,5-Bis(4-ethylphenyl)-2-imidazolyl]methyl]-N-(2,6-dimethylphenyl)-1-piperazineacetamide Trihydrochloride Hydrate and 4-[[4,5-Bis(4-ethylphenyl)-2-oxazolyl]methyl]-N-(2,6-dimethylphenyl)-1-piperazineacetamide Dihydrochloride Hydrate (Method B):

A solution of bromoacetyl chloride (2.00 mL, 24.2 mmol) in anhydrous dichloromethane (20 mL) was added dropwise to a cold (0° C.) mixture of 2-hydroxy-1,2-di-(4-ethylphenyl)ethanone (IX; 6.5 g, 24.2 mmol) and N-methylmorpholine (NMM; 2.7 mL, 24.2 mmol) in anhydrous dichloromethane (180 mL). The mixture was stirred at 0° C. for 1 h and at ambient temperature for 2 h before additional 2-hydroxy-1,2-di-(4-ethylphenyl)ethanone (0.5 mL) and NMM (0.6 mL) were added to aid in completion. After 1 h, the mixture was washed with saturated sodium bicarbonate solution, 1$\underline{N}$ HCl and brine. Following drying and solvent evaporation, the residue was purified by flash chromatography on silica gel (gradient elution with 10% ethyl acetate in hexanes followed by 25% ethyl acetate in hexanes) and furnished 6.10 g (65%) of bromoacetoxy-1,2-di-(4-ethylphenyl)ethanone as a pale-yellow oil which was carried on directly. A portion of bromoacetoxy-1,2-di-(4-ethylphenyl)ethanone (3.15 g, 8.09 mmol) was treated with anhydrous sodium carbonate (0.86 g, 8.09 mmol), sodium iodide (0.12 g) and N-(2,6-dimethylphenyl)-1-piperazineacetamide (2.0 g, 8.09 mmol) in anhydrous acetonitrile (120 mL) and the resulting mixture was heated to 80° C. for 5 h before it was cooled and concentrated down in vacuo. Purification of the residue by flash chromatography on silica gel with absolute ethyl acetate gave 3.40 g (76%) of 2-oxo-1,2-di-(4-ethylphenyl)ethyl 4-[[[(2,6-dimethylphenyl) amino]carbonyl]-methyl]-1-piperazineacetate as pale-yellow foam. A portion of 2-oxo-1,2-di-(4-ethylphenyl)ethyl 4-[[[(2,6-dimethylphenyl)amino]carbonyl]-methyl]-1-piperazineacetate (2.50 g, 4.50 mmol) was dissolved in glacial acetic acid (75 mL) and ammonium acetate (1.65 g, 22.5 mmol) was added. The mixture was gently refluxed under nitrogen for 6 h before the solvent was removed in vacuo. The residue was partitioned between ethyl acetate and 1$\underline{N}$ sodium hydroxide solution (until basic) and the organic phase was separated, washed with brine, dried and concentrated. The residue was purified by flash chromatography on silica gel (gradient elution with ethyl acetate followed by 10% methanol in ethyl acetate) and yielded 0.61 g (22%) of the oxazole product I as a white solid and 0.85 g (30%) of the imidazole product I as a white solid after salt formation with ethereal hydrogen chloride.

For the oxazole: m.p. 134°–156° C. (sealed tube); $^1$H NMR (300 MHz, DMSO-d$_6$) δ 10.43 (s, 1H), 7.44 (d, J=7.9 Hz, 4H), 7.28 (d, J=8.0 Hz, 4H), 7.06 (s, 3H), 4.33 (s, 2H), 4.20 (s, 2H), 3.52–2.90 (series of m, 8H), 2.65–2.58 (m, 4H), 2.14 (s, 6H), 1.17 (t, J=7.5 Hz, 6H); $^{13}$C NMR (75 MHz, DMSO-d$_6$/D$_2$O) ppm 162.51, 145.97, 142.13, 135.18, 132.39, 128.45, 128.01, 127.94, 127.71, 123.86, 55.97, 51.84, 50.05, 48.46, 27.73, 17.47, 14.85; IR (KBr) 3422, 3176, 2964, 2932, 2354, 1688, 1538, 1522, 1498, 1474, 1456, 1444, 1414, 1374, 1298, 1060, 964, 836, 772 cm$^{-1}$; MS (DCI) m/z 537.

Anal. Calc'd for C$_{34}$H$_{40}$N$_4$O$_2$°1.6HCl°0.5H$_2$O: C, 67.61; H, 7.11; N, 9.28; Cl, 9.39; H$_2$O, 1.49; Found: C, 67.59; H, 7.03; N, 9.11; Cl, 9.35; H$_2$O, 1.68.

For the imidazole: m.p. 185°–195° C. (sealed tube); $^1$H NMR (300 MHz, DMSO-d$_6$) δ 10.32 (s, 1H), 7.50 (d, J=7.9 Hz, 4H), 7.29 (d, J=8.3 Hz, 2H), 7.24 (d, J=8.3 Hz, 2H), 4.32–4.30 (m, 4H), 3.58–3.07 (series of m, 8H), 2.66–2.57 (m, 4H), 2.15 (s, 6H), 1.17 (t, J=7.5 Hz, 6H); $^{13}$C NMR (75 MHz, DMSO-d$_6$/D$_2$O) ppm 163.09, 157.00, 146.08, 145.59, 144.60, 135.16, 133.88, 132.72, 128.27, 128.09, 127.91, 127.54, 127.35, 126.43, 124.96, 56.32, 51.75, 51.07, 48.55, 27.81, 27.77, 17.63, 15.02; IR (KBr) 3422, 3176, 2966, 2932, 2872, 2560, 1690, 1636, 1530, 1496, 1456, 1416, 1374, 1304, 1240, 836, 772 cm$^{-1}$;.

Anal. Calc'd for C$_{34}$H$_{41}$N$_5$O°2.3HCl°0.6H$_2$O: C, 64.78; H, 7.12; N, 11.11; Cl, 12.94; Found: C, 64.48; H, 7.03; N, 10.83; Cl, 13.05.

EXAMPLE 26

2-(aminocarbonyl)-$\underline{N}$-(4-amino-2,6-dichlorophenyl)-4-[(4,5diphenyloxazolyl)methyl]-1-piperazineacetamide (I)

A mixture of 2-(aminocarbonyl)-$\underline{N}$-(4-amino-2,6-dichlorophenyl)-1-piperazineacetamide trifluoroacetate (1.38 g, 2.0 mmol), 4,5-diphenyl-2-bromomethyloxazole (72% pure, 875 mg, 2.0 mmol), and K$_2$CO$_3$ (4.0 g) in 20 mL of DMF was stirred at room temperature for 15 minutes. The resulting mixture was partitioned between ethyl acetate-hexane and water, the organic extract dried, and solvent removed in vacuo to yield a crude residue of 1.27 g. This material was subjected to flash chromatography on deactivated silica gel (from a slurry of 300 g of silica gel in methylene chloride containing 3.4 mL of conc. NH$_4$OH). The product was eluted with CH$_2$Cl$_2$:MeOH:NH$_4$OH 97.4:2.0:0.6, yielding a residue of 970 mg which was triturated in methanolether to yield a white solid (638 mg, 55% yield): m.p. 137°–139° C.; $^1$H NMR (300 MHz, DMSO-d$_6$) δ 2.83–3.27 (m, 7H), 3.32 (s, 2H), 3.81 (s, 2H), 5.67 (s, 2H), 6.64 (s, 2H), 7.28 (s, 2H), 7.40–7.49 (m, 6H), 7.55–7.63 (m, 4H), 9.44 (s, 1H); MS (FAB) m/z 579 (M+);

Anal. calc'd for C$_{29}$H$_{28}$N$_6$O$_3$Cl$_2$°H$_2$O: C, 58.30; H, 5.06; N, 14.07; Found: C, 58.06; H, 4.92; N, 13.87;

EXAMPLE 27

N-(4-amino-2,6-dichlorophenyl)-4-[(4,5-diphenyloxazolyl)methyl]-1-piperazineacetamide (Method A)

A mixture of $\underline{N}$-(4-amino-2,6-dichlorophenyl)-1-piperazinecarboxamide (370 mg, 1.22 mmol), 4,5-diphenyl-2-bromomethyloxazole (530 mg, 1.22 mmol), and K$_2$CO$_3$ (700 mg) in 20 mL of DMF was stirred at room temperature for 15 minutes, then partitioned between ethyl acetate and water. The ethyl acetate extract was dried and the solvent removed in vacuo to yield a crude residue of 900 mg. This was reecrystallized in methylene chloride-ether to yield a white solid (312 mg, 48% yield): m.p.>203° C. (dec.); $^1$H NMR (300 MHz, DMSO-d$_6$) δ 2.50–2.65 (m, 8H), 3.05 (s, 2H), 3.75 (s, 2H), 5.63–5.64 (s, 2H), 6.60 (s, 2H), 7.34–7.47 (m, 6H), 7.52–7.58 (m, 4H), 9.14 (s, 1H); MS (DCI) m/z 536 (M+);

Anal. calc'd for C$_{28}$H$_{27}$N$_5$O$_2$Cl$_2$°0.25H$_2$O: C, 62.17, H, 5.12, N, 12.95, Found: C, 62.13, H, 5.05, N, 12.89.
(Method B)

A mixture of (6.0 g, 0.015 mol) oxazolylpiperazine (XXXIV; see Example 20); anhydrous $K_2CO_3$ (3 equivalents) and 2,6-dichloro-4-nitro-α-bromoacetamide (5.01 g, 0.015 mol) in 150 ml of $CH_3CN/DMF$ (1:1) was stirred for 10–20 h. The solvent was removed in vacuo and the residue was taken up in $CH_2Cl_2$ or $CHCl_3$ and washed with water and brine. The organic layer was dried and concentrated to give 4.0 g of a yellow solid which was used without any further purification. MS (DCI) MH+ 566.

This nitro intermediate (3.90 g, 0.0068 mol) was then taken up in 100 ml of methanol or ethanol and hydrogenated in a Parr shaker at 50–60 psi, room temperature for 4–10 h with 0.5 g of 5% Pt/S/C as catalyst. Filtration of the catalyst followed by evaporation of the solvent and purification through a silica gel column using $CH_3OH/CHCl_3$ (2:98) as eluent provided 3.45 g of the free base (95%) of the title compound.

Appropriate modification of the foregoing procedures result in production of other Formula I products. These modifications would be familiar to one skilled in the art. Some additional Formula I compounds prepared in this manner are set forth below.

EXAMPLE 28

2-Aminocarbonyl-N-(2,6-dimethylphenyl)-4-[(4,5-diphenyl-2-oxazolyl)methyl]-1-piperazineacetamide Dihydrochloride Hydrate (I)

Obtained 0.78 g (55%), pale-yellow crystalline solid, m.p. 166°–176° C. (sealed tube); $^1H$ NMR (300 MHz, DMSO-$d_6$) δ 9.94 (br s, 1H), 8.23 (br s, 1H), 7.81 (br s, 1H), 7.61–7.58 (m, 4H), 7.51–7.36 (m, 6H), 7.08 (s, 3H), 4.34 (m, 2H), 4.14 (m, 1H), 3.87 (m, 2H), 3.54–3.21 (3m, 5H), 2.15 (s, 6H); $^{13}C$ NMR (75 MHz, DMSO-$d_6$) ppm 174.59, 169.63, 161.45, 147.06, 137.01, 136.56, 136.14, 133.55, 130.75, 130.43, 130.01, 129.38, 129.14, 128.26, 67.60, 60.59, 56.53, 55.14, 53.11, 52.84, 19.87; IR (KBr) 3414, 3020, 2466, 1688, 1504, 1476, 1444, 1378, 1072, 1026, 964, 766, 696 cm$^{-1}$; MS (DCI) m/z 524.

Anal. Calc'd for $C_{31}H_{33}N_5O_3$°2.0HCl°1.0H$_2$O°0.3Et$_2$O: C, 60.73; H, 6.33; N, 11.00; H$_2$O, 2.83. Found: C, 60.41; H, 5.93; N, 11.08; H$_2$O, 2.57.

EXAMPLE 29

N-(2,6-Dimethylphenyl)-4-[(4,5-diphenyl-2-thiazolyl)methyl]-1-piperazineacetamide Dihydrochloride Hydrate (I)

Obtained 0.80 g (58%), off-white solid, m.p. 149°–166° C. (decomp. pt. 195° C., sealed tube); $^1H$ NMR (300 MHz, DMSO-$d_6$) δ 10.37 (s, 1H), 7.47–7.44 (m, 2H), 7.39–7.37 (m, 3H), 7.35–7.29 (m, 5H), 7.07 (s, 3H), 4.47 (br s, 2H), 4.33 (s, 2H), 3.60 (br s, 4H), 3.39–3.32 (m, 4H), 2.16 (s, 6H); $^{13}C$ NMR (75 MHz, DMSO-$d_6$/D$_2$O) ppm 163.22, 161.95, 149.24, 135.19, 134.60, 133.51, 132.74, 130.59, 129.12, 128.98, 128.84, 128.55, 128.46, 128.37, 127.92, 127.55, 56.39, 55.83, 50.70, 48.81, 17.64; IR (KBr) 3422, 2966, 2362, 1684, 1538, 1498, 1474, 1440, 760, 698 cm$^{-1}$; MS m/z Anal. calc'd for $C_{30}H_{33}N_4OS$: 497.2375, found 497.2364. Anal. Calc'd for $C_{30}H_{32}N_4OS$°1.7HCl°0.2H$_2$O: C, 64.09; H, 6.11; N, 9.97; H$_2$O, 0.64; Found: C, 64.12; H, 6.07; N, 9.92; H$_2$O, 0.60.

EXAMPLE 30

4-[(2-Benzimidazolyl)methyl)]-N-(2,6-dimethylphenyl)-1-piperazine acetamide Trihydrochloride Hydrate (I)

Obtained 0.78 g (53%), m.p. 200°–230° C. (sealed tube); $^1H$ NMR (300 MHz, DMSO-$d_6$) δ 10.47 (s, 1H), 7.82–7.79 (m, 2H), 7.53–7.50 (m, 2H), 7.07 (s, 3H), 4.34 (s, 2H), 4.27 (s, 2H), 3.52 (br m, 8H), 3.11 (m, 2H), 2.89 (m, 2H), 2.16 (s, 6H); $^{13}C$ NMR (75 MHz, DMSO-$d_6$/D$_2$O) ppm 162.43, 150.18, 135.19, 132.53, 130.37, 127.96, 127.68, 126.18, 113.76, 55.97, 51.89, 51.07, 48.78, 17.57; IR (KBr) 3422, 3176, 2966, 2856, 1688, 1622, 1538, 1474, 1460, 1442, 1388, 1340, 1292, 990, 752, 622 cm$^{-1}$; MS m/z calc'd for $C_{22}H_{28}N_5O$: 378.2294, found 378.2290.

Anal. Calc'd for $C_{22}H_{27}N_5O$°2.5HCl°0.7H$_2$O°0.14Et$_2$O: C, 55.12; H, 6.62; N, 14.25; H$_2$O, 2.57; Found: C, 55.36; H, 6.44; N, 14.09; H$_2$O, 2.34.

EXAMPLE 31

N-(2,6-Dimethylphenyl)-4-[(4,5-diphenyl-2-imidazolyl)methyl]-1-piperazineacetamide Dihydrochloride Hydrate Obtained 0.26 g (32%), off-white solid, m.p. 195°–210° C. (dec., sealed tube); $^1H$ NMR (300 MHz, DMSO-$d_6$)δ 10.41 (s, 1H), 7.52–7.51 (m, 4H), 7.44–7.43 (m, 6H), 7.06 (s, 3H), 4.30 (s, 2H), 4.17 (s, 2H), 3.51 (m, 2H), 3.34 (m, 2H), 3.18 (m, 2H), 2.86 (m, 2H), 2.14 (s, 6H); $^{13}C$ NMR (75 MHz, DMSO-$d_6$/D$_2$O) ppm 162.49, 142.59, 135.17, 132.62, 129.74, 129.13, 128.24, 128.08, 127.95, 127.62, 126.65, 56.01, 51.79, 50.15, 48.50, 17.61; IR (KBr) 3422, 3176, 2956, 2836, 2682, 2562, 1690, 1638, 1602, 1538, 1476, 1444, 1368, 1284, 766, 696 cm$^{-1}$; MS m/z calc'd for $C_{30}H_{34}N_5O_1$: 480.2763, found 480.2753.

Anal. Calc'd for $C_{30}H_{33}N_5O$°2.1HCl°0.8H$_2$O: C, 63.15; H, 6.48; N, 12.27; H$_2$O, 2.53. Found: C, 63.30; H, 6.36; N, 12.26; H$_2$O, 2.35.

EXAMPLE 32

2,6-(Dimethylphenyl)-4-[4,5-bis(4-methoxyphenyl)-2-oxazolyl)methyl]-1-piperazineacetamide Dihydrochloride Obtained 0.31 g (9%), white solid, m.p. 229°–235° C. (dec., sealed tube); $^1H$ NMR (300 MHz, DMSO-$d_6$) δ 10.33 (s, 1H), 7.54–7.49 (m, 4H), 7.07 (s, 3H), 7.05–6.96 (m, 4H), 4.43 (br s, 2H), 4.34 (br s, 2H), 3.79 (s, 3H), 3.77 (s, 3H), 3.69–3.65 (m, 4H), 3.54–3.37 (m, 4H), 2.16 (s, 3H); $^{13}C$ NMR (75 MHz, DMSO-$d_6$) ppm 162.70, 159.83, 159.19, 154.72, 145.63, 135.08, 133.85, 133.59, 128.64, 128.31, 127.80, 126.94, 123.82, 120.38, 114.50, 114.18, 55.91, 55.34, 55.21, 50.87, 49.60, 47.95, 18.23; IR (KBr) 3422, 3258, 3228, 2940, 2352, 1704, 1610, 1540, 1520, 1498, 1446, 1304, 1248, 1176, 1022, 956, 826 cm$^{-1}$; MS m/z calc'd for $C_{32}H_{37}N_4O_4$: 541.2815, found 541.281.

Additional Formula I compounds, synthesized by modifications of the foregoing synthetic procedures, are set forth in Table I.

TABLE I
Additional Products of Formula I

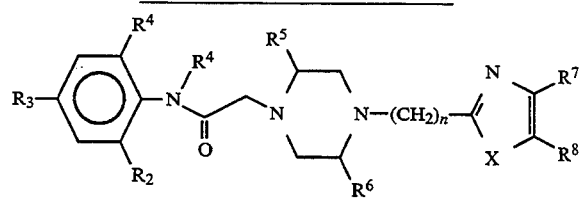

| Ex. # | R1 | R2 | R3 | R4 | R5 | R6 | R7=R8 | n | X | mp (°C.) |
|---|---|---|---|---|---|---|---|---|---|---|
| 33 | Me | Me | H | H | H | H | Ph | 1 | O | 165-170[1] |
| 34 | Me | Me | H | H | H | COOEt | Ph | 1 | O | 118-112[1] |
| 35 | Me | Me | H | H | H | H | p-F—Ph | 1 | O | 189-191[2] |
| 36 | Me | Me | H | H | H | H | p-CF3—Ph | 1 | O | 159-161[2] |
| 37 | Me | Me | H | H | H | H | m-CL—Ph | 1 | O | 174-76[2] |
| 38 | Me | Me | H | H | H | H | Ph | 3 | O | 220-25[1] |
| 39 | Me | Me | H | H | H | H | Ph | 4 | O | 140-45[1] |
| 40 | Me | Me | H | H | H | H | Ph | 4 | S | 222-224[1] |
| 41 | Me | Me | H | H | —(CH2)— | | Ph | 1 | O | 165-170[1] |
| 42[4] | Me | Me | H | H | O(H) | H(O) | Ph | 1 | O | 75-95[3] |
| 43 | Cl | Cl | NH2 | H | H | CONH2 | Ph | 1 | O | 206-8[1] |
| 44 | H | H | H | H | H | H | Ph | 1 | O | 161-65[2] |
| 45 | H | H | Cl | H | H | H | Ph | 1 | O | 176-174[2] |
| 46 | H | H | F | H | H | H | Ph | 1 | O | 171-75[2] |
| 47 | H | H | OMe | H | H | H | Ph | 1 | O | 166-170[2] |
| 48 | H | H | Me | H | H | H | Ph | 1 | O | 164-165[2] |
| 49 | Cl | Cl | H | H | H | H | Ph | 1 | O | 176-179[2] |

[1] Hcl Salt
[2] Maleate Salt
[3] Free base
[4] A mixture of (2:1) 2-oxo and 3-oxo piperazine derived product

Further Detailed Description of the Invention

Some additional compounds of Formula I have been made and tested and have been found to have the pharmacologic profile that, as described supra, would make them useful antiischemic agents. These compounds are described more fully in the following examples and in Table II, infra, and were prepared by utilizing appropriate modifications of the foregoing synthetic procedures.

A chiral synthetic procedure was also developed to provide single enantiomers of certain stereoisomeric compounds of Formula I. The procedure is illustrated in Scheme III. This synthesis results in a Formula I compound with a chiral center in the piperazine ring. Utilization of this scheme resulted in isolation of the single enantiomers for a preferred compound of the present series: R-(+)- and S-(−)-2-(aminocarbonyl)-4-[(4,5-diphenyl-2-oxazolyl)methyl]-N-(4-amino-2,6-dichlorophenyl)-1-piperazineacetamide. While both enantiomers were neuroprotective, the S-(−)-enantiomer had about 30 times the activity of the R-(+)-enantiomer.

Scheme III
Chiral Synthetic-Procedure

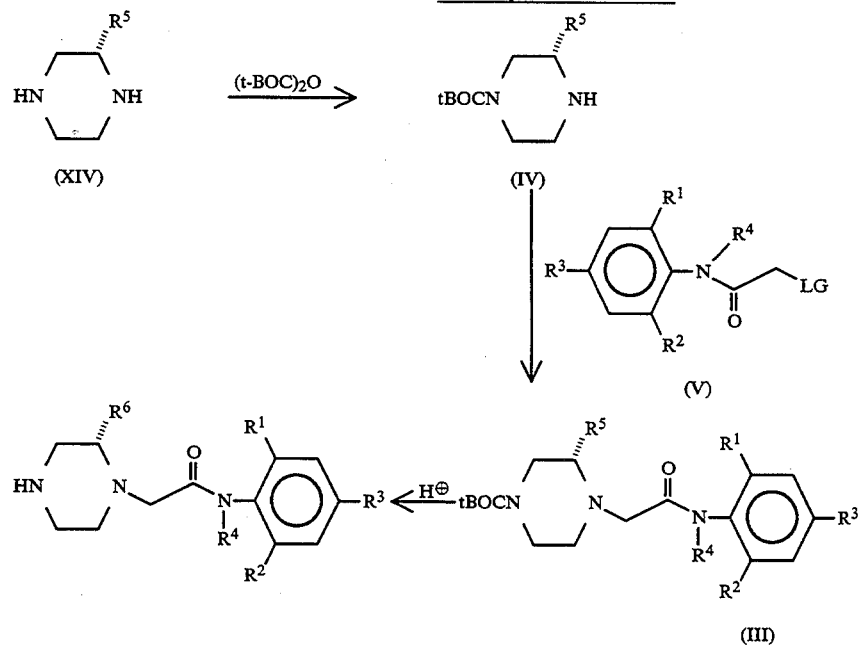

-continued
Scheme III
Chiral Synthetic-Procedure
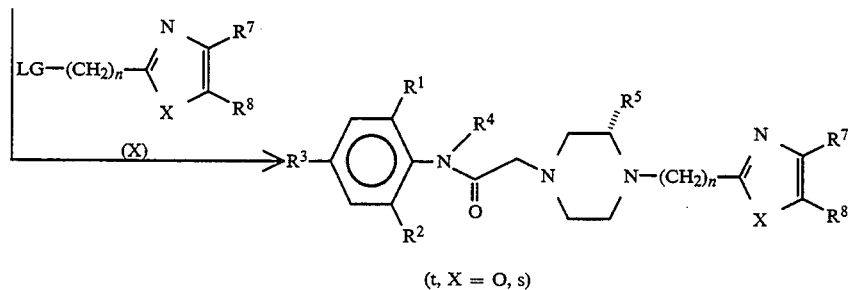
(t, X = O, s)
Preparation of the single enantiomers of the specific piperazine starting material is shown in Scheme IV.
Scheme IV
Preparation of Enantiomer Piperazines
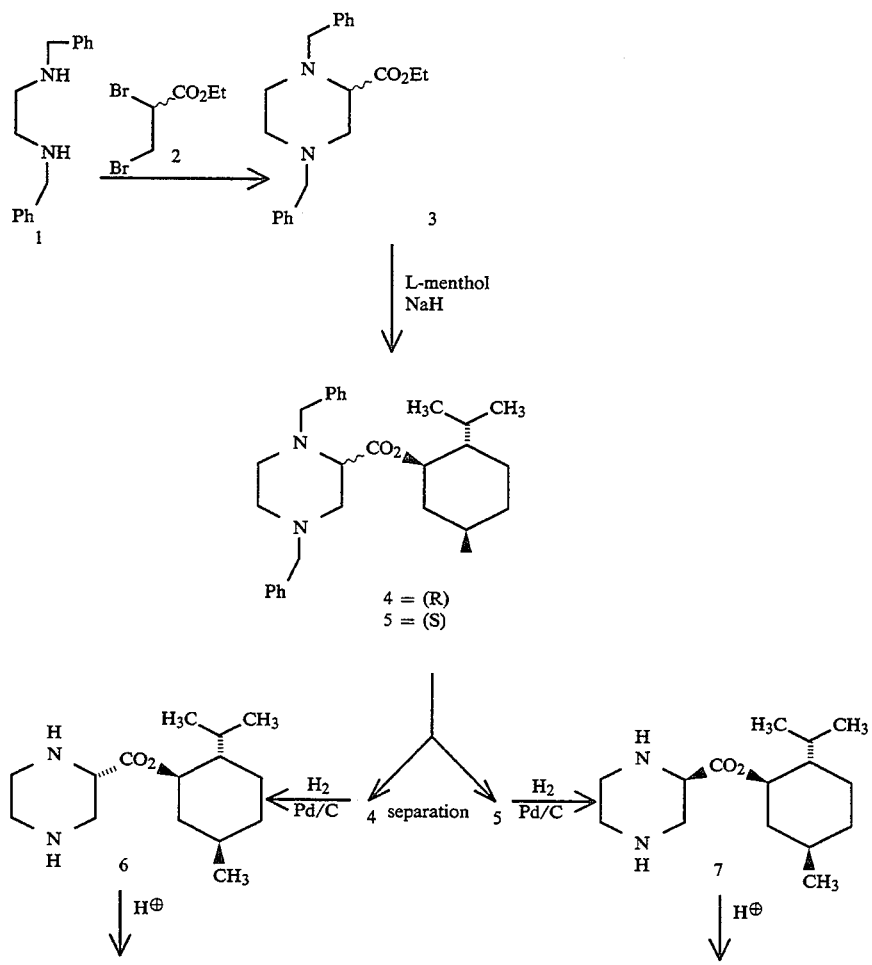

Scheme IV
Preparation of Enantiomer Piperazines

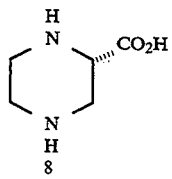

8

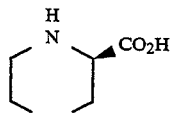

9

| NH₃

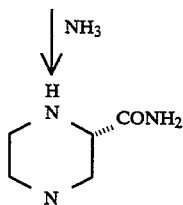

10

| NH₃

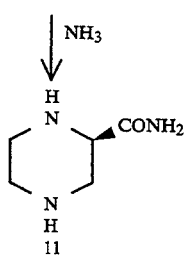

11

Chiral Synthesis of Enantiomeric Piperazine Compounds of Formula I

EXAMPLE 50

R-(+)-Piperazine-2-Carboxamide (10)

A. Ethyl N,N'-di(phenylmethyl)-piperazine-2-carboxylate (3)

To a solution of 1 (N,N'-dibenzylethylenediamine, 76.8 g, 0.296 mol) in toluene (240 mL) at 40° C. with mechanical stirring was added dropwise a solution of 2 (ethyl 2,3-dibromopropionate, 71.0 g, 0.296 mol) and triethylamine (84 mL, 0.60 mol) in 75 mL of toluene such that the temperature remained below 80° C. The mixture was stirred at 80° C. for 2.5 hours, then cooled. The resulting mixture was filtered, and the filtrate partitioned with 200 mL of water. The organic extract was dried with $Na_2SO_4$, and solvent removed in vacuo to yield an amber oil (3, 105 g, 100% yield). This material was used as is in the subsequent step, thus analysis was not obtained.

B.  L-Menthyl-R-(+)-N,N'-di(phenylmethyl)piperazine-2-carboxylate hydrochloride monohydrate (4)

A mixture of 3 (94.25 g, 0.264 mol), L-menthol (53.6 g, 0.343 mol), and NaH (2.0 g, 60% suspension in mineral oil) in 150 mL of toluene was distilled with the gradual addition of toluene as needed. This was continued for 1.5 hours. The mother liquor was then stirred in a mixture of 2N HCl (170 mL) and diethyl ether (800 mL) for 30 minutes. The resulting precipitate was then collected by filtration and washed with ether, followed by 1N HCl, yielding a white solid (83.0 g). A second crop crystallized afer standing overnight (12.6 g). The first crop was fractionally recrystallized in 400 mL ethanol and 240 mL 0.2N HCl, adding 80 mL of 0.2N HCl to the mother liquor each time a further crystallization was carried out. Six crops were collected by this method. Optical rotation was used to determine optical purity relative to literature values.

4: The first three crops consisted primarily of R-isomer, and were combined.

Obtained: a white solid (40.0 g, 30% yield); m.p. 152°–167° C.; ¹H NMR (300 MHz, DMSO-d₆): δ 0.56–0.59 (d, j=6.9 Hz, 3H), 0.74–0.76 (d, j=6.9 Hz, 3H), 0.83–0.86 (d, j=6.3 Hz, 3H), 0.93–1.04 (q, j=11.7 Hz, 3H), 1.31–1.43 (m, 2H), 1.57–1.62 (m, 3H), 1.87–1.90 (d, j=11.7 Hz, 1H), 2.66–2.72 (m, 2H), 3.03–3.24 (m, 4H), 3.40 (s, 3H), 3.70–3.82 (dd, j=14.4, 10.2 Hz, 2H), 4.43–4.48 (m, 2H), 4.61–4.67 (dt, j=6.9, 3.6 Hz, 1H), 7.26–7.32 (m, 5H), 7.43 (s, 3H), 7.61 (s, 2H); ¹³C NMR (75 MHz, DMSO-d₆): δ 15.45, 20.49, 21.80, 22.41, 25.44, 30.82, 33.53, 46.06, 46.42, 49.93, 50.77, 57.77, 58.57, 61.94, 75.10, 127.46, 128.32, 128.72, 128.83, 129.46, 131.50, 136.66, 168.69; IR (KBr): 1730, 1275, 755, 700 cm⁻¹; MS (DCI): m/z 449; [α]D²⁰ +18.73 (c=1.0, CHCl₃); analysis calc'd. for $C_{29}H_{40}N_2O_2 \cdot HCl \cdot H_2O$: C, 69.23; H, 8.61; N, 5.57; found: C, 69.51; H, 8.57; N, 5.56.

C. L-Menthyl-R-(−)-piperazine-2-carboxylate dihydrochloride (6)

A mixture of 4 (21.8 g, 0.0434 mol) and 10% Pd/C (2.6 g) in 200 mL of ethanol was hydrogenated in a Parr apparatus at 40–50 psi for 18 hours. Catalyst was then removed by filtration, and the filtrate concentrated in vacuo. To the residue was added 1N HCl in ether (25 mL) combined with 50 mL of ethanol. This mixture was stirred vigorously for 30 minutes, then a white solid was collected by filtration (12.7 g, 86% yield); m.p.>225° C. (dec.); ¹H NMR (300 MHz, DMSO-d₆): δ 0.67–0.70 (d, j=6.9 Hz, 3H), 0.84–0.88 (dd, j=5.7, 0.9 Hz, 6H), 1.03–1.10 (m, 2H), 1.38–1.45 (t, j=11.4 Hz, 2H), 1.61–1.65 (d, j=10.5 Hz, 2H), 1.78–1.89 (dsept, j=6.9, 2.7 Hz, 1H), 1.91–1.95 (m, 1H), 3.19–3.50 (m, 6H), 3.65–3.71 (dd, j=9.9, 3.3 Hz, 1H), 4.58–4.63 (dd, j=8.4, 3.6 Hz, 1H), 4.67–4.76 (dt, j=6.6, 4.5 Hz, 1H), 10.29 (br s, 3H); 13C NMR (75 MHz, DMSO-d₆): δ 15.78, 20.73, 21.11, 21.83, 22.40, 25.26, 30.75, 33.49, 40.57, 46.07, 51.89, 76.63, 164.56; IR (KBr): 3600–2300, 1745, 1370, 1250 cm⁻¹; MS (DCI): m/z 269; [α]D²⁰ −50.34 (c=1.1 H₂O); analysis calc'd. for $C_{15}H_{28}N_2O_2 \cdot 2.3\ HCl$: C, 51.15; H, 8.67; N, 7.95; found: C, 51.07; H, 8,70; N, 7.59.

D. R-(+)-piperazine-2-carboxylic acid dihydrochloride (8)

A solution of 6 (12.7 g, 0.0372 mol) in 100 mL of 6N HCl was refluxed 6 hours, then cooled, and 200 mL of diethyl ether was added. The resulting mixture was stirred 30 minutes, and a white solid collected by filtration (6.53 g, 86% yield); m.p.>255° C. (dec.); ¹H NMR (300 MHz, D₂O): δ 3.29–3.47 (m, 3H), 3.59–3.71 (m, 2H), 3.85–3.90 (m, 1H), 4.25–4.30 (m, 1H); ¹³C NMR (75 MHz, D₂O): δ 42.14, 42.48, 44.63, 56.00, 170.18; IR (KBr): 3100–2400, 1760, 1216, 926 cm⁻¹; MS (DCI): m/z 131; [α]D²⁰ +3.89 (c=1.2, 2N HCl); analysis calc'd. for $C_5H_{10}N_2O_2 \cdot 2\ HCl$: C, 29.57; H, 5.96; N, 13.80; found: C, 29.74; H, 5.94; N, 13.80.

E. R-(+)-Piperazine-2-carboxamide (10)

A solution of 8 (6.98 g, 0.0344 mol) in 200 mL of methanol containing 30% aqueous $NH_3$ (4.6 mL, 0.069 mol) was refluxed 24 hours with DOWEX 50W-X8 200-mesh, H+ form cation-exchange resin (42 g, 92 meq). The resin was collected by filtration and resuspended in 200 mL of methanol. This suspension was then cooled to 0° C., and $NH_3$ was bubbled into solution (9.50 g, 0.560 mol). The flask was then sealed, and stirred at room temperature for 3 days. The resin was then collected by filtration, and placed in a column, and eluted with 150 mL of $2\underline{N}$ aqueous $NH_3$. The filtrate and eluate were combined, solvent removed in vacuo, and remaining water removed azotropically with n-propanol. The residue was then purified on Amberlite CG-400, 200 mesh hydroxide form anion exchange resin, eluting 10 with water, and eluting unreacted 8 with $1\underline{N}$ HCl. Solvent was removed azeotropically with n-propanol, yielding a white solid (3.23 g, 73% yield); m.p. 140°-148°; $^1$H NMR (300 MHz, DMSO-$d_6$): δ 2.37-2.60 (m, 4H), 2.69-2.75 (m, 1H), 2.83-2.88 (m, 1H), 2.98-3.02 (m, 1H), 6.96 (br s, 1H), 7.10 (br s, 1H); IR (KBr): 3600-2700, 1680, 1600 cm$^{-1}$; MS (DCI) m/z 130; $[\alpha]D^{20}$ +27.27 (c=1.35, EtOH); Analysis calc'd. for $C_5H_{11}N_3O$: C, 46.49; H, 8.58; N, 32.53; found: C, 46.26; H, 8.59; N, 32.18.

EXAMPLE 51

(S)-(−)-Piperazine-2-carboxamide (11)

A. L-Menthyl-S-(−)-N,N'-di(phenylmethyl)piperazine-2-carboxylate dihydrochloride (5)

Step B-E of Example 49 are repeated using the residual material of Step A of Example 49.

The remaining three crops consisted primarily of S-isomer and were combined with the original second crop. Obtained: a white solid (36.0 g, 26% yield); m.p. 165°-171° C.; $^1$H NMR (300 MHz, DMSO-$d_6$) δ 0.65-0.67 (d, j=6.6 Hz, 3H), 0.84-0.86 (d, j=6.0 Hz, 6H), 0.93-1.18 (q, j=8.7 Hz, 3H), 1.41-1.45 (m, 2H), 1.60-1.64 (d, j=10.5 Hz, 2H), 1.82-1.86 (m, 2H), 2.64-2.71 (m, 1H), 2.98-3.26 (m, 4H), 3.39-3.46 (m, 1H), 3.77-3.80 (m, 3H), 4.29-4.34 (m, 2H), 4.65-4.68 (m, 1H), 7.29-7.31 (m, 5H), 7.42 (s, 3H), 7.59-7.61 (m, 2H); $^{13}$C NMR (75 MHz, DMSO-$d_6$) δ 15.75, 20.56, 21.84, 22.60, 25.71, 30.80, 33.56, 46.15, 46.30, 49.11, 50.97, 57.49, 58.38, 62.17, 75.13, 127.54, 128.35, 128.70, 128.98, 129.52, 131.66, 168.59; IR (KBr) 1735, 1200, 750, 700 cm$^{-1}$; $[\alpha]D^{20}$ −104.45 (c=1.0, CHCl$_3$); HRMS (FAB): m/z calc'd for $C_{29}H_{41}N_2O_2$: 449.3168; found: 449.3183.

L-Menthyl S-(−)-Piperazine-2-carboxylate dihydrochloride. (7)

White solid, m.p. 249°-251° (dec., sealed tube); $^1$H NMR (300 MHz, DMSO-$d_6$) δ 10.26 (br s, 3H), 4.76-4.68 (m, 1H), 4.63-4.58 (m, 1H), 3.65-3.60 (m, 1H), 3.51-3.21 (series of m, 7H), 1.92-1.83 (m, 2H), 1.64-1.60 (m, 2H), 1.43-1.36 (m, 2H), 1.09-0.98 (m, 3H), 0.85 (t, J=6.6 Hz, 6H), 0.69 (d, J=6.9 Hz, 3H); $^{13}$C NMR (75 MHZ, DMSO-$d_6$) δ 164.77, 76.50, 55.99, 51.93, 46.14, 40.77, 33.48, 30.75, 25.36, 22.66, 21.82, 20.62, 18.56, 16.14, 15.78; IR (KBr) 3440, 2956, 2872, 2742, 2696, 2588, 1744, 1454, 1388, 1370, 1354, 1282, 1066, 984, 964, 944, 932 cm$^{-1}$; MS (DCI) m/z 269; $[\alpha]D^{20}$ −56.08° (c=1.2, 2N HCl); analysis calc'd for $C_{15}H_{28}N_2O_2\cdot 2HCl\cdot 0.6H_2O$: C, 51.17. H, 8.93. N, 7.96. Cl, 20.14. $H_2O$, 3.07. Found: C, 51.06; H, 8.68; N, 7.83; Cl, 20.32.

C. S-(−)-Piperazine-2-carboxylic Acid dihydrochloride (9)

White solid, 8.68 g (94%), m.p. 274°-276° (dec., sealed tube); $^1$H NMR (300 MHz, D$_2$O) δ 10.37 (v br m, 3H), 4.39 (dd, J=11.6, 3.8 Hz, 1H), 3.65 (dd, J=13.3, 3.7 Hz, 1H), 3.49-3.35 (m, 2H), 3.33-3.14 (series of m, 3H); $^{13}$C NMR (75 MHz, DMSO-$d_6$) δ 166.54, 52.04, 41.11; IR (KBr) 3026, 2982, 2806, 1758, 1552, 1532, 1434, 1408, 1392, 1244, 1216, 1098, 1056, 940, 926, 830, 636, 536 cm$^{-1}$; MS (DCI) m/z 131; $[\alpha]D^{20}$ −3.17° (c=1.0, 2N HCl); analysis calc'd for $C_5H_{10}N_2O_2\cdot 2HCl$: C, 29.57. H, 5.96. N, 13.80. Cl, 34.92. Found: C, 29.60; H, 5.84; N, 13.71; Cl, 35.11.

D. S-(−)-Piperazine-2-carboxamide. (11)

White solid, 3.18 g (59%), m.p. 138°-141°; $^1$H NMR (300 MHz, DMSO-$d_6$) δ7.14 (br s, 1H), 7.00 (br s, 1H), 3.03 (dd, J=9.3, 3.1 Hz, 1H), 2.91-2.87 (m, 1H), 2.77-2.40 (series of m, 7H); $^{13}$C NMR (75 MHz, DMSO-$d_6$) δ 174.24, 59.12, 49.42, 46.02, 45.28; IR (KBr) 3352, 3312, 3192, 2972, 2948, 2910, 2830, 1678, 1616, 1414, 1310, 1138, 1120, 912, 842 cm$^{-1}$; MS (DCI) m/z 130; $[\alpha]D^{20}$ −21.73° (c=1.8, EtOH); analysis calc'd for $C_5H_{11}N_3O$: C, 46.50. H, 8.58. N, 32.53. Found: C, 46.13; H, 8.51; N, 32.15.

EXAMPLE 52

A. R-(−)-(1,1-dimethylethoxycarbonyl)-2-piperazinecarboxamide (XIV-enantiomer)

A solution of 10 (prepared in Example 49; 7.40 g, 0.574 mol) in 150 mL of methanol at room temperature was stirred for 1 hour with the gradual addition of di-tertbutyl dicarbonate (12.5 g, 0.0574 mol). Solvent was removed in vacuo, and the residue passed through a silica gel plug, eluting with CH$_2$Cl$_2$:MeOH 95:5 to 85:15. Solvent was removed in vacuo to yield the t-BOC derivative as a white solid (11.4 g, 87% yield); m.p. 125°-130°; $^1$H NMR (DMSO-$d_6$): δ 1.39 (s, 9H), 2.57-2.64 (m, 1H), 2.84-2.93 (m, 3H), 3.20-3.23 (m, 1H), 3.30-3.35 (m, 1H), 3.65-3.69 (m, 1H), 3.90-3.95 (m, 1H), 7.27 (br s, 1H), 7.47 (br s, 1H); IR (KBr): 34−−, 1690, 1650, 1370, 1270, 1150; MS (DCI): m/z 230; $[\alpha]D^{20}$ −19.40 (c=1.0, EtOH); analysis calc'd for $C_{10}H_{19}N_3O_3\cdot 0.25$ $H_2O$: C, 51.38; H, 8.41; N, 17.97; found: C, 51.36; H, 8.11; N, 17.83.

B. S-(+)-(1,1-dimethylethoxycarbonyl)-2-piperazinecarboxamide (XIV-enantiomer)

Similarly, the t-BOC derivative of 11 (Ex. 50) was prepared.

White solid, 4.55 g (89%), m.p. 134°-136°; $^1$H NMR (300 MHz, DMSO-$d_6$) δ 7.27 (br s, 1H), 7.12 (br s, 1H), 3.83 (m, 1H), 3.63-3.59 (m, 1H), 3.06-3.01 (m, 1H), 2.84-2.72 (m, 3H), 2.54-2.49 (m, 2H), 1.39 (s, 9H); $^{13}$C NMR (75 MHz, DMSO-$d_6$) δ 172.82, 153.87, 78.81, 57.78, 46.37, 43.89, 28.07; IR (KBr) 3366, 3252, 3002, 2990, 2976, 2940, 2924, 2862, 1686, 1646, 1406, 1368, 1270, 1222, 1172, 1154, 890 cm$^{-1}$; MS (DCI) m/z 230; $[\alpha]D^{20}$ +22.88° (c=1.2, EtOH); analysis calc'd for $C_{10}H_{19}N_3O_3$: C, 52.39. H, 8.35. N, 18.33. Found: C, 52.19; H, 8.27; N, 18.25.

EXAMPLE 53

A. R-(+)-2-(aminocarbonyl)-N-(4-nitro-2,6-dichlorophenyl)-4-(1,1-dimethylethoxycarbonyl)-1-piperazineacetamide (III)

A solution of the R-(−)-enantiomer (XIV prepared in Example 51-A: 4.7 g, 0.0205 mol), N-(4-nitro-2,6-dichlorophenyl)-2-bromoacetamide (6.8 g, 0.0207 mol), and triethylamine (3.2 mL, 0.023 mol) in 100 mL of DMF was stirred at room temperature for 4 hours. The solution was then added to 900 mL of ethyl acetate, filtered, and the filtrate partitioned with pH 5 biphthalate buffer 0.5M (2×400 mL), followed by water (2×400 mL). The organic extract was dried over $Na_2SO_4$ and solvent removed in vacuo. The residue was dissolved in $CH_2Cl_2$ and filtered through a silica gel plug, eluting unreacted starting bromoacetamide with $CH_2Cl_2$, and eluting 15 with $CH_2Cl_2$:MeOH 90:10. Solvent was removed in vacuo to yield a light tan solid (7.50 g, 77% yield); m.p. 115°–120°; $^1H$ NMR (300 MHz, $CDCl_3$): δ 1.47 (s, 9H), 2.50–2.60 (m, 1H), 3.05–3.40 (m, 5H), 3.56–3.61 (m, 1H), 3.82–3.87 (m, 1H), 4.05–4.10 (m, 1H), 5.80 (br s, 1H), 6.35 (br s, 1H), 8.26 (s, 2H); IR (KBr): 1700, 1675, 1535, 1345, 1250 cm$^{-1}$; MS (DCI): m/z 476; $[α]D^{20}$ +32.19 (c=1.0, $CHCl_3$); Chiral HPLC: 78% ee; Analysis calc'd for $C_{18}H_{23}N_5O_6Cl_2$: C, 45.39; H, 4.87; N, 14.70; found: C, 45.27; H, 4.89; N, 14.53.

B. S-(−)-2-(aminocarbonyl)-N-(4-nitro-2,6-dichlorophenyl)-4-(1,1-dimethylethoxycarbonyl)-1-piperazineacetamide (III)

Similarly, the S-(−)-enantiomeric compound was prepared from the XIV intermediate obtained in Example 51-B.

Pale, yellow foam, 8.20 g (90%), m.p. 102°–105°; $^1H$ NMR (300 MHz, DMSO-$d_6$) δ 10.16 (s, 1H), 8.40 (s, 2H), 7.64 (s, 1H), 7.34 (s, 1H), 3.69–3.65 (m, 2H), 3.33 (s, 1(?)), 3.23–2.99 (m, 5H), 2.42–2.36 (m, 1H), 1.39 (s, 9H); $^{13}C$ NMR (75 MHz, DMSO-$d_6$) δ 172.08, 168.48, 153.55, 146.27, 139.24, 134.27, 123.57, 79.12, 64.23, 59.77, 58.32(?), 54.92, 50.20, 45.56, 41.69, 28.01; IR (KBr) 3268, 3096, 2978, 2934, 1698, 1538, 1482, 1428, 1390, 1366, 1346, 1268, 1246, 1168, 1148, 1126, 812, 758, 742 cm$^{-1}$; MS (DCI) m/z 476; $[α]D^{20}$ −23.09° (c=1.6, EtOH); analysis calc'd for $C_{18}H_{23}Cl_2N_5O_6$.0.35EtOAc.0.08$CH_3CN$.0.11$CH_2Cl_2$.0.10$H_2O$: C, 45.30. H, 5.11. N, 13.64. $H_2O$, 0.35. Found: C, 44.95; H, 4.96; N, 13.44; $H_2O$.

EXAMPLE 54

A. R-(+)-2-(aminocarbonyl)-N-(4-amino-2,6-dichlorophenyl)-4-(1,1-dimethylethoxycarbonyl)-1-piperazineacetamide (III)

A mixture of the product of Example 52A (7.35 g, 0.0154 mol), 5% Pt/C (3.25 g), and 4% methanolic thiophene (1.5 mL) in 150 mL of methanol was hydrogenated in a Parr apparatus at 50° C. and 50 psi for 2 hours. Catalyst was removed by filtration, and solvent removed in vacuo from the filtrate, yielding a white solid (6.73 g, 93% yield); m.p.>135 (dec.); $^1H$ NMR (300 MHz, DMSO-$d_6$): δ 1.40 (s, 9H), 2.28–2.34 (m, 1H), 2.89–3.32 (m, 6H), 3.66–3.76 (m, 2H), 5.68 (s, 2H), 6.65 (s, 2H), 7.63 (s, 1H), 7.95 (s, 1H), 9.46 (s, 1H); IR (KBr): 3400–3300, 1700, 1670, 1370, 1260 cm$^{-1}$; MS (DCI): m/z 446; $[α]D^{20}$ +30.33 (c=1.2, EtOH); Analysis calc'd for $C_{18}H_{25}N_5O_4Cl_2$.0.5$H_2O$.0.5 $CH_4O$: C, 47.14; H, 5.99; N, 14.86; found: C, 47.08; H, 5.53; N, 14.77.

B. S-(−)-2-(aminocarbonyl)-N-(4-amino-2,6-dichlorophenyl)-4-(1,1-dimethylethoxycarbonyl)-1-piperazineacetamide (III)

In similar fashion the product of Example 52B was hydrogenated to give off-white foam, 7.0 g (93%), m.p. 155°–160°; $^1H$ NMR (300 MHz, DMSO-$d_6$) δ 9.47 (s, 1H), 7.64 (s, 1H), 7.32 (s, 1H), 6.64 (s, 2H), 5.68 (s, 2H), 3.70–3.65 (m, 2H), 3.26–2.88 (series of m, 6H), 2.32–2.26 (m, 1H), 1.39 (s, 9H); $^{13}C$ NMR (75 MHz, DMSO-$d_6$) δ 172.22, 168.76, 153.53, 149.31, 133.88, 119.44, 112.47, 79.12, 64.84, 58.29, 50.23, 45.35, 28.02; IR (KBr) 3448, 3350, 2978, 2932, 1684, 1598, 1504, 1462, 1426, 1366, 1270, 1246, 1168, 1126, 802 cm$^{-1}$; MS (DCI) m/z 446; $[α]D^{20}$ −26.99° (c=0.95, EtOH); Analysis calc'd for $C^{18}H_{25}Cl_2N_5O_4$.0.10$H_2O$: C, 48.25. H, 5.67. N, 15.63. $H_2O$, 0.40. Found: C, 47.96; H, 5.57; N, 15.24; $H_2O$.

EXAMPLE 55

A. R-(+)-2-(aminocarbonyl)-N-(4-amino-2,6-dichlorophenyl)-1-piperazineacetamide trihydrochloride (II)

A solution of the protected acetamide intermediate prepared in Example 53A (6.55 g, 0.0147 mol) in 20 mL of methanol and 80 mL of ethyl acetate was combined with 200 mL of 1N HCl in ether. The resulting mixture was stirred at room temperature for 2 hours, the solvent reduced to 50 mL in vacuo, and 50 mL of diethyl ether added. The resulting precipitate was collected by filtration. This was recrystallized in methanol:acetonitrile 1:3 to yield a white solid (5.3 g, 79% yield), m.p. 190–215 (dec.); $^1H$ NMR (300 MHz, DMSO-$d_6$): δ 2.90–2.95 (m, 1H), 3.10–3.47 (m, 7H), 3.62–3.64 (m, 1H), 6.84 (s, 2H), 7.66 (s, 1H), 7.98 (s, 1H), 9.24 (br s, 1H), 9.64 (br s, 1H), 9.75 (s, 1H); IR (KBr): 3700–3200, 1690, 1600, 1530 cm$^{-1}$; MS (DCI): m/z 346; $[α]D^{20}$ +17.94 (c=1.0, $H_2O$); analysis calc'd for $C_{13}H_{17}N_5O_2Cl_2$.3 HCl: C, 34.27; H, 4.43; N, 15.37; found: C, 34.31; H, 4.69; N, 15.34.

B. S-(−)-2-(aminocarbonyl)-N-(4-amino-2,6-dichlorophenyl)-1-piperazineacetamide Trihydrochloride (II)

In similar fashion the S-enantiomeric intermediate was de-protected to give off-white solid, 5.88 g (87%), m.p. 222°–226° (dec., sealed tube); $^1H$ NMR (300 MHz, $D_2O$) δ 7.51 (s, 2H), 3.72 (dd, J=8.4, 3.5 Hz, 1H), 3.66–3.23 (series of m, 7H), 3.00–2.90 (m, 1H); $^{13}C$ NMR (75 MHz, $D_2O$) δ 175.00, 174.10, 137.71, 134.54, 133.97, 126.08, 62.83, 59.52, 49.68, 46.67, 44.86; IR (KBr) 3378, 3268, 3136, 2916, 2810, 2592, 1706, 1542, 1470, 1416, 1376, 968, 810, 596 cm$^{-1}$; MS (DCI) m/z 346; $[α]D^{20}$ −3.67° (c=1.1, $H_2O$); analysis calc'd for $C_{13}H_{17}Cl_2N_5O_2$.2.95HCl.1.5$H_2O$: C, 32.48. H, 4.81. N, 14.57. Cl, 36.50. $H_2O$, 5.62. Found: C, 32.64; H, 4.55; N, 14.57; Cl, 36.60; $H_2O$, 12.57.

EXAMPLE 56

A. R-(+)-2-(aminocarbonyl)-N-(4-amino-2,6-dichlorophenyl)-4-[(4,5-diphenyl-2-oxazolyl)methyl]-1-piperazineacetamide trihydrochloride monohydrate (I)

A mixture of the compound II prepared in Example 54A (5.0 g, 0,011 mol) in 100 mL of acetonitrile containing triethylamine (6.4 mL, 0.046 mol) was stirred at room temperature until fully dissolved. To this was added 2-bromomethyl-4,5-diphenyloxazole (3.46 g, 0.011 mol), and the resulting mixture was stirred at room temperature for 4 hours. Solvent was removed in vacuo, and the residue was partitioned between $CH_2Cl_2$ (100 mL) and saturated aqueous $NaHCO_3$ (75 mL). The organic extract was washed with water (2×50 mL), then dried over $Na_2SO_4$ and solvent removed in vacuo. The residue was subjected to flash chromatography, and the product was eluted with $CH_2Cl_2$:MeOH:$NH_2OH$ 98.8:1.0:0.2 to 98.2:1.5:0.3, yielding a light yellow solid (3.17 g, 50% yield). Optical purity was determined to be 74% ee by chiral HPLC. Fractional recrystallization in absolute ethanol resulted in enrichment of the R-enantiomer in the mother liquors by precipitating racemate. Solvent was removed in vacuo from the enriched mother liquor, and the residue was partitioned between MeOH:$H_2O$ 70:30 (100 mL)

and CH₂Cl₂ (5×10 mL), removing most colored impurities. Solvent was removed in vacuo from the water-methanol extract, and the residue was subjected to flash chromatography, using previous conditions, yielding an off-white solid (1.10 g). This was dissolved in a mixture of CH₂Cl₂ and methanol, to which was added 1$\underline{N}$ HCl in ether (6.0 mL). Solvent was removed in vacuo to yield an off-white solid (100% ee, 1.15 g, 15% yield); m.p.>185 (dec.); ¹H NMR (300 MHz, DMSO-d₆): δ 3.15–3.25 (m, 2H), 3.35–3.45 (m, 3H), 3.49–3.54 (m, 1H), 3.70 (br s, 2H), 3.97–4.02 (m, 1H), 4.40 (br s, 2H), 5.75 (s, 1H), 6.76 (s, 2H), 7.33–7.51 (m, 6H), 7.57–7.60 (m, 4H), 7.77 (s, 1H), 8.10 (s, 1H), 9.89 (br s, 1H); ¹³C NMR (75 MHz, DMSO-d₆): 48.36, 51.43, 54.95, 113.74, 126.71, 127.42, 127.87, 128.56, 128.82, 129.09, 129.44, 131.37, 133.73, 134.85, 146.26, 147.61; IR (KBr): 3700–1900, 1700, 770, 700 cm⁻¹; MS (DCI): m/z 579; [α]D²⁰ +15.80 (c=0.9, EtOH); analysis calc'd for C₂₉H₂₈N₆O₃Cl₂.3 HCl.H₂O: C, 49.28; H, 4.71; N, 11.89; found: C, 49.29; H, 4.66; N, 11.76.

B. (S-(−)-2-(aminocarbonyl)-N-(4-amino-2,6-dichlorophenyl)-4-[(4,5-diphenyl-2-oxazolyl)methyl]-1-piperazineacetamide Trihydrochloride (I)

In a similar manner the S-enantiomeric product was prepared as white solid (100% ee, 99.6% overall purity), 1.50 g (17%), m.p. 200°–210° br m, 8H), 7.03 (s, 2H), 4.47 (s, 2H), 4.04–4.02 (m, 1H), 3.75–3.56 (2 m, 3H), 3.42–3.25 (m, 5H); ¹³C NMR (75 MHz, DMSO-d₆/D₂O) δ 169.97, 168.21, 153.79, 146.96, 144.26, 134.93, 133.91, 130.69, 129.74, 129.04, 128.87, 127.48, 127.22, 126.60, 122.36, 115.60, 60.99, 55.79, 51.29, 50.81, 49.25, 47.42; IR (KBr) 3394, 3160, 2956, 2842, 2570, 1698, 1604, 1526, 1504, 1470, 1444, 1414, 1384, 1358, 766, 696 cm⁻¹; MS (DCI) m/z 579; [α]D²⁰ −18.68° (c=1.0, EtOH); analysis calc'd for C₂₉H₂₈N₆O₃Cl₂.1.6HCl.0.9H₂O: C, 53.26; H, 4.84; N, 12.85; Cl, 19.52; H₂O, 2.48. Found: C, 53.22; H, 4.74; N, 12.80; Cl, 19.50; H₂O, 2.34.

EXAMPLE 57

4-[2-Benzimidazolyl)methyl)-N-(2,6-dimethylphenyl)-1-piperazineacetamide Trihydrochloride Hydrate Etherate. (I)

Using 2-benzimidazolylmethyl bromide as the compound X starting material was obtained 0.78 g (33%) of the title compound as a pale yellow solid, m.p. 200°–230° C. (sealed tube); ¹H NMR (300 MHz, DMSO-d₆ δ 10.47 (s, 1H), 7.82–7.79 (m, 2H), 7.53–7.50 (m, 2H), 7.07 (s, 3H), 4.34 (s, 2H), 4.27 (s, 2H), 3.52 (br m, 8H), 3.11 (m, 2H), 2.89 (m, 2H), 2.16 (s, 6H); ¹³C NMR (75 MHz DMSO-d₆/D₂O) ppm 162.43, 150.18, 135.19, 132.53, 130.37, 127.96, 127.68, 126.18, 113.76, 55.97, 51.89, 51.07, 48.78, 17.59; IR (KBr) 3422, 3176, 2966, 2856, 1688, 1622, 1538, 1474, 1460, 1442, 1388, 1340, 1292, 990, 752, 622 cm⁻¹; MS m/c calc'd for C₂₂H₂₈N₅O: 378.2294, found 378.2290. Anal. Calc'd for C₂₂H₂₇N₅O.2.5HCl.0.7H₂O.0.14Et₂O: C, 55.12; H, 6.62; N, 14.25; H₂O, 2.57. Found C, 55.36; H, 6.44; N, 14.09; H₂O, 2.34.

EXAMPLE 58

4-[(2-benzoxazolyl)methyl]-N-(2,6-dimethylphenyl)-1-piperazineacetamide Maleate (1:2.75)

1.45 g of the intermediate piperazineacetamide of Example 15 in acetonitrile (30 ml); 3 g K₂CO₃; a catalytic amount of KI and 1eq (0.95 g, 4.53 mMol) of bromomethylbenzoxazole was stirred 24 hrs, filtered, and the solvents evaporated. The residue was dissolved in MeOH, made acidic with maleaic acid and allowed to crystalize. Filtration gave 1.67 g product 53% yield; mp 163°–165° C.; ¹HNMR (300 MHz DMSO-d₆) δ 9.81 (s, 1H), 7.74 (m, 2H) 7.41 (m, 2H), 7.07 (m, 3H), 4.09 (s, 2H), 4.02 (s, 2H), 3.28 (s, 4H), 2.90 (s, 4H), 2.13 (s, 6H); ¹³C NMR (75 MHz DMSO-d₆) δ 166.96(0), 162.41(0), 150.30(0), 140.49(0), 135.05(0), 133.80(0), 133.36(+), 127.85(+), 127.00(+), 125.40(+), 124.59(+), 119.76(+), 110.89(+), 56.64(−), 53.17(−), 51.80(−), 48.95(−), 18.07(+); IR (KBr) 3392, 1696, 1620, 1574, 1518, 1468, 1454, 1428, 1356, 1218, 1082, 990, 868; MS (DCI) m/e 379; Analysis calc'd for C₂₂H₂₆N₄O₂.2.75C₄H₄O₄: C, 56.81 H, 5.35 N, 8.03; found: C, 56.52 H, 5.34 N, 8.39.

EXAMPLE 59

(1S, 4S) N-(2,6-dimethylphenyl)-5-[(3,4-diphenyl-2-oxazolyl)-methyl]-2,5-diazabicyclo[2.2.1]preptane-2-acetamide dihydrochloride.

The 2,5-diazabicyclo [2.2.1] heptane (2 mmoless; prepared as described in WO88/02627) was alkylated with the intermediate of Example 7, 2-bromo-N-(2,6-dimethylphenyl)acetamide, in 20 mL of DMF with K₂CO₃ as base. The desired mono-alkylated product was purified by column chromatography and further alkylated with 2-bromomethyl-4,5-diphenyloxazole in DMF (20 mL) with K₂CO₃ as a base. The product was isolated and purifed by column chromatography. Anhydrous HCl in ether was used to prepare the corresponding dihydrochloride salt. m.p. (165°–170°).

EXAMPLE 60

N-(2,6-dimethylphenyl)-4-[(4,5-diphenyl-2-oxazolyl)-methyl]-1,4-diazabicyclo[2.2.1]octane-1-acetamide.

Employing similar experimental procedure described above, 1,4-diazabicycle [2.2.2] octane (cf: J.Het. Chem. 11, 449 (1974)) was converted to the title compound. m.p. 154°–185° (HCl salt).

TABLE II

Further Products of Formula I

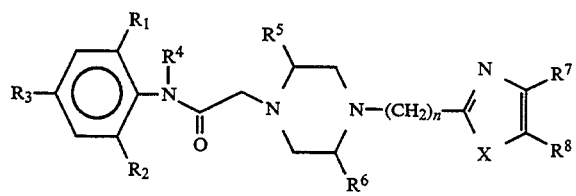

| Ex. # | R¹ | R² | R³ | R⁴ | R⁵ | R⁶ | R⁷ | R⁸ | X | n | mp |
|---|---|---|---|---|---|---|---|---|---|---|---|
| 61 | Cl | Cl | NHCO(CH₂)₃—COMe | H | H | H | Ph | Ph | O | 1 | 74–75 |
| 62 | Cl | Cl | NHCO(CH₂)₃—COMe | H | CONH₂ | H | Ph | Ph | O | 1 | 118–121 |
| 63 | Cl | Cl | NH₂ | H | (R) CONH₂ | H | Ph | Ph | O | 1 | 195–200 |
| 64 | Cl | Cl | NH₂ | H | (S) CONH₂ | H | Ph | Ph | O | 1 | 200–210[1] |
| 65 | Cl | Cl | H | H | CONH₂ | H | Ph | Ph | O | 1 | 172–198[1] |
| 66 | H | CH₃ | H | H | H | H | Ph | Ph | O | 1 | 166–171[2] |
| 67 | H | Cl | H | H | H | H | Ph | Ph | O | 1 | 176–178[2] |
| 68 | CH₃ | CH₃ | H | H | H | H | 4(CH₃)₂N—Ph | Ph | NH | 1 | 95–110[2] |
| 69 | CH₃ | CH₃ | H | H | H | H | 4(CH₃)₂N—Ph | Ph | O | 1 | 183–186[2] |
| 70 | CH₃ | CH₃ | H | H | CO₂Me | H | Ph | Ph | O | 1 | 135–158[1] |
| 71 | Cl | Cl | NH₂ | H | CONH₂ | H | 4F—Ph | 4F—Ph | O | 1 | 152–155[2] |
| 72 | Cl | Cl | NO₂ | H | CONH₂ | H | Ph | Ph | O | 1 | 120[2] |
| 73 | Cl | Cl | NO₂ | H | H | H | Ph | Ph | O | 1 | 135–138[2] |
| 74 | CH₃ | CH₃ | H | H | H | H | H | Ph | O | 1 | 154–161[2] |
| 75 | CH₃ | CH₃ | H | H | H | H | Ph | H | O | 1 | 166–167[2] |
| 76 | CH₃ | CH₃ | H | CH₃ | H | H | Ph | Ph | O | 1 | 179–180[2] |
| 77 | CH₃ | CH₃ | H | H | H | H | 4BrPh | 4BrPh | O | 1 | 172–173 |

[1]HCl Salt
[2]Maleate Salt

I claim:

1. A Compound of Formula I

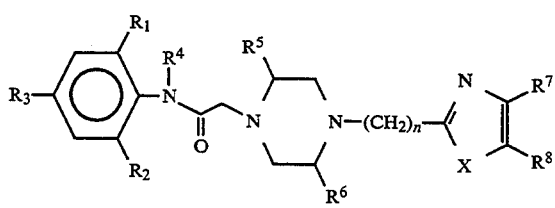

and the pharmaceutically acceptable acid addition salt or hydrate thereof wherein R¹ and R² are independently selected from hydrogen, C₁₋₄ alkyl, C₁₋₄ alkoxy, halogen and trifluoromethyl;

R³ is hydrogen, halogen, C₁₋₄ alkoxy, nitro or —NR⁹R¹⁰ with R⁹ and R¹⁰ being independently selected from hydrogen or C₁₋₄ alkyl, alkanoyl and

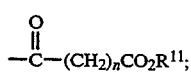

R⁴ is hydrogen or C₁₋₄ alkyl;

R⁵ and R⁶ are independently selected from hydrogen, —CONR⁶R¹⁰, oxo and —CO₂R¹¹ with R¹¹ being C₁₋₄ alkyl, or R⁵ and R⁶ can be taken together to form a methylene or ethylene bridge;

R⁷ and R⁸ taken together is a butylene or are both

with R¹² being hydrogen, halogen, trifluoromethyl, C₁₋₄ alkyl or C₂₋₄ alkyl-N(R⁴)₂;

n is zero or an integer from 1 to 4; and

X is S, O, or NH.

2. A compound of claim 1 wherein X is S.

3. A compound of claim 1 wherein X is O.

4. A compound of claim 1 wherein X is NH.

5. A compound of claim 1 wherein R¹ and R² are selected from methyl and chloro.

6. A compound of claim 1 wherein n is 1.

7. A compound of claim 1 wherein R⁷ and R⁸ are phenyl.

8. A compound of claim 1 selected from the group consisting of N-(2,6-dimethylphenyl)-4-[(4,5-diphenyl-2-oxazolyl)methyl]-1-piperazineacetamide; N-(2,6-dichlorophenyl)-4-[(4,5-diphenyl-2-oxazolyl)methyl]-1-piperazineacetamide; 4-[[4,5-bis(4-ethylphenyl)-2-oxazolyl]methyl]-N-(2,6-dimethylphenyl)-1-piperazineacetamide; 4-[[4,5-bis(4-fluorophenyl)-2-oxazolyl]methyl]-N-(2,6-dimethylphenyl)-1-piperazineacetamide; 4-[[4,5-bis[4-(trifluoromethyl)phenyl]-2-oxazolyl]methyl]-N-(2,6-dimethylphenyl)-1-piperazineacetamide; 4-[[4,5-bis(3-chlorophenyl)-2-oxazolyl]methyl]-N-(2,6-dimethylphenyl)-1-piperazineacetamide; 4-[[4,5-diphenyl-2-oxazolyl]e- thyl]-N-(2,6-dimethylphenyl)-1-piperazineacetamide; N-(2,6-dimethylphenyl)-4-[4-(4,5-diphenyl-2-oxazolyl)-propyl]-1-piperazineacetamide; N-(2,6-dimethylphenyl)-4-[4-(4,5-diphenyl-2-oxazolyl)butyl]-1-piperazineacetamide; N-(4-amino-2,6-dichlorophenyl)-4-[(4,5-diphenyl oxazolyl)methyl]-1-piperazineacetamide; 4-[(4,5-diphenyl-2-oxazolyl)methyl]-N-phenyl-1-piperazineacetamide; N-(4-chlorophenyl)-4-[(4,5-diphenyl-2-oxazolyl)methyl]-1-piperazineacetamide; 4-[(4,5-diphenyl-2-oxazolyl)methyl]-N-(4-fluorophenyl)-1-piperazineacetamide; 4-[(4,5-diphenyl-2-oxazolyl)methyl]-N-(4-methoxylphenyl)-1-piperazineacetamide; 4-[(4,5-diphenyl-2-oxazolyl)methyl]-N-(4-methylphenyl)-1-piperazineacetamide; N-(2,6-dichlorophenyl-4-[(4,5-diphenyl-2-oxazolyl)methyl]-1-piperazineacetamide; 2,6-dimethylphenyl-4-[[4,5-(4-methoxyphenyl)-2-oxazolyl]methyl]-1-piperazineacetamide.

9. The compound of claim 8, N-(4-amino-2,6-dichlorophenyl)-4-[(4,5-diphenyl-2-oxazolyl)methyl]-1-piperazineacetamide.

10. A compound of claim 1 selected from the group consisting of 4-[[4,5-bis(4-ethylphenyl)-2-imidazolyl]-methyl-N-(2,6-dimethylphenyl)-1-piperazineacetamide; N-(2,6-dimethylphenyl)-4-[(4,5-diphenyl-2-imidazolyl)-methyl]-1-piperazineacetamide; N-(2,6-dimethylphenyl)-4-[4-(4,5-diphenyl-2-thiazolyl)butanyl]-1-piperazineacetamide; N-(2,6-dimethylphenyl)-4-[(4,5-diphenyl-2-thiazolyl)methyl]-1-piperazineacetamide.

11. A compound of claim 1 selected from the group consisting of ethyl-4-[[[(2,6-dimethylphenyl)amino]carboxymethyl]-1-[(4,5-diphenyl-2-oxazolyl)methyl)-2-piperazinecarboxylate; 2-aminocarbonyl-4-[[4,5 diphenyl-2-oxazolyl]methyl]-N-(2,6-dimethylphenyl)-1-piperazineacetamide; (1S, 4S) N-(2,6-dimethylphenyl)-5-[(4,5-diphenyl-2-oxazolyl)methyl]-2,5-diazabicyclo[2,2,1]heptane-2-acetamide; 2-aminocarbonyl N-(2,6-dimethylphenyl)-4-[[4,5-diphenyl-2-oxazolyl)methyl]-1-piperazineacetamide; 3-(aminocarbonyl)-N-(4-amino-2,6-dichlorophenyl)-4-[(4,5-diphenyl(-2-oxazolyl)methyl-1-piperazineacetamide; 2-aminocarbonyl-N-(4-amino-2,6-dichlorophenyl,-4-[(4,5-diphenyloxazolyl)-methyl-1-piperazineacetamide.

12. The compound of claim 11, 2-aminocarbonyl-4-[(4,5-diphenyl-2-oxalyl)methyl]-N-(4-amino-2,6-dichlorophenyl)-1-piperazineacetamide.

13. A process for protecting CNS and cardiac tissue from ischemia which comprises administering an effective ischemia-protective amount of a compound of claim 1 to a mammal susceptible to or suffering from ischemia.

14. The process of claim 13 wherein the claim 1 compound is N-(4-amino-2,6-dichlorophenyl)-4-[(4,5-diphenyl-2-oxazolyl)methyl]-1-piperazineacetamide.

15. An antiischemic pharmaceutical composition, suitable for systemic administration to a mammal, comprising a pharmaceutical carrier and a compound of claim 1.

16. The antiischemic pharmaceutical composition of claim 15 wherein the claim 1 compound is N-(4-amino-2,6-dichlorophenyl)-4-[(4,5-diphenyl-2-oxazolyl)methyl]-1-piperazineacetamide.

* * * * *